United States Patent
Saito et al.

(10) Patent No.: US 11,131,621 B2
(45) Date of Patent: Sep. 28, 2021

(54) ANALYSIS DEVICE AND ANALYSIS METHOD

(71) Applicant: JVC KENWOOD Corporation, Yokohama (JP)

(72) Inventors: Atsushi Saito, Yokohama (JP); Shigehiko Iwama, Yokohama (JP); Masahiro Yamamoto, Yokohama (JP)

(73) Assignee: JVC KENWOOD CORPORATION, Yokohama (JP)

( * ) Notice: Subject to any disclaimer, the term of this patent is extended or adjusted under 35 U.S.C. 154(b) by 325 days.

(21) Appl. No.: 16/178,889

(22) Filed: Nov. 2, 2018

(65) Prior Publication Data
US 2019/0145885 A1 May 16, 2019

(30) Foreign Application Priority Data

Nov. 10, 2017 (JP) .............................. JP2017-217036

(51) Int. Cl.
*G01N 21/17* (2006.01)
*B82Y 15/00* (2011.01)
(Continued)

(52) U.S. Cl.
CPC ............ *G01N 21/01* (2013.01); *B01L 3/5027* (2013.01); *B82Y 15/00* (2013.01); *G01N 15/1456* (2013.01); *G01N 21/17* (2013.01); *G01N 21/253* (2013.01); *G01N 33/53* (2013.01); *G01N 35/00069* (2013.01); *G01N 35/04* (2013.01);
(Continued)

(58) Field of Classification Search
None
See application file for complete search history.

(56) References Cited

U.S. PATENT DOCUMENTS

2004/0248093 A1* 12/2004 Coombs ............ B01L 3/502761
435/6.11
2018/0321227 A1* 11/2018 Iwama ............. G01N 33/54346

FOREIGN PATENT DOCUMENTS

JP       2002-39974 A    2/2002
JP       2017058242 A    3/2017
(Continued)

OTHER PUBLICATIONS

Extended European Search Report dated Apr. 11, 2019, for counterpart European application No. 18205272.0.
(Continued)

*Primary Examiner* — Neil N Turk
(74) *Attorney, Agent, or Firm* — Nath, Goldberg & Meyer; Jerald L. Meyer

(57) ABSTRACT

An analysis device includes an optical disc drive, a gate information processing unit, a detection circuit, and a gate shift processing unit. The optical disc drive rotates a specimen analysis disc and detects a measurement radial position for an optical pickup. The detection circuit generates gate signals shifted by a gate shift amount in each measurement radial position in a rotating direction of the specimen analysis disc, and generates count values of the respective gate signals. The gate shift processing unit divides a gate signal-corresponding region of the corresponding gate signal by a unit gate shift amount in the rotating direction of the specimen analysis disc to define a plurality of divided regions and sets count values of the divided regions based on the count values of the gate signals.

5 Claims, 18 Drawing Sheets

(51) Int. Cl.
G01N 33/543 (2006.01)
G01N 33/53 (2006.01)
G01N 21/01 (2006.01)
G01N 35/04 (2006.01)
G01N 35/00 (2006.01)
G01N 15/14 (2006.01)
G01N 21/25 (2006.01)
B01L 3/00 (2006.01)

(52) U.S. Cl.
CPC ............... *G01N 2015/1486* (2013.01); *G01N 2021/0162* (2013.01); *G01N 2021/1791* (2013.01); *G01N 2035/0441* (2013.01); *G01N 2035/0491* (2013.01)

(56) References Cited

FOREIGN PATENT DOCUMENTS

| JP | 2017-138186 A | 8/2017 |
|---|---|---|
| WO | 2017/134944 A1 | 8/2017 |

OTHER PUBLICATIONS

Japanese Office Action dated Mar. 2, 2021 corresponding to application No. 2017-217036.

* cited by examiner

14

14

ANALYSIS DEVICE AND ANALYSIS METHOD

CROSS REFERENCE TO RELATED APPLICATION

This application is based upon and claims the benefit of priority under 35 U.S.C. § 119 from Japanese Patent Application No. 2017-217036, filed on Nov. 10, 2017, the entire contents of which are incorporated herein by reference.

BACKGROUND

The present disclosure relates to an analysis device and an analysis method of analyzing biomaterials such as antigens and antibodies.

Immunoassays are known to quantitatively analyze disease detection and therapeutic effects by detecting particular antigens or antibodies as biomarkers associated with diseases.

Patent Document 1 (JP2017-58242) discloses an analysis device in which antibodies that are fixed to a reaction region on a specimen analysis disc, are allowed to bind to antigens provided on nanoparticles to be analyzed in a specimen, and the antigens are labeled by nanoparticles for labeling (hereinafter referred to as "nanoparticles") having antibodies and are scanned with laser light emitted from an optical pickup so as to detect the nanoparticles captured on the reaction region. The analysis device disclosed in Patent Document 1 is an optical disc device utilized for detecting a specimen.

The conventional analysis device as disclosed in Patent. Document 1 moves the optical pickup per track in a radial direction of the specimen analysis disc being rotated. The analysis device generates a plurality of gate signals for dividing the reaction region at regular time intervals in the rotating direction of the specimen analysis disc, and detects the nanoparticles captured on the reaction region per gate signal. The analysis device indirectly measures the nanoparticles captured on the reaction region by counting the number of the nanoparticles detected, so as to indirectly measure a distribution of the nanoparticles in the reaction region.

While the conventional analysis device has a measurement resolution equivalent to a track pitch in the radial direction of the specimen analysis disc, the measurement resolution is determined depending on a gate width of a gate signal in the rotating direction of the specimen analysis disc. A decrease in the gate width of the gate signal can improve the measurement resolution. However, as the gate width is decreased, the number of gate signals generated in the rotating direction of the specimen analysis disc is increased, resulting in an increase in circuit scale.

SUMMARY

According to a first aspect of the embodiments, there is provided an analysis device including: an optical disc drive including an optical pickup configured to irradiate, with laser light, a reaction region formed in a circular specimen analysis disc with nanoparticles captured and receive reflected light to generate a light reception detection signal, and a reference position detection sensor configured to detect a reference position defining portion formed in the specimen analysis disc to generate a reference position detection signal, the optical disc drive being configured to rotate the specimen analysis disc, move the optical pickup in a radial direction of the specimen analysis disc, and detect a measurement radial position for the optical pickup in the specimen analysis disc to generate measurement radial positional information; a gate information processing unit configured to generate gate information including a gate shift amount based on the measurement radial positional information; a detection circuit configured to generate a gate signal shifted by the gate shift amount in each measurement radial position in a rotating direction of the specimen analysis disc in accordance with the reference position detection signal and the gate information, extract nanoparticle pulse signals generated every time the nanoparticles are scanned with the laser light, from the light reception detection signal per gate signal, and count the nanoparticle pulse signals to generate a count value of the corresponding gate signal; and a gate shift processing unit configured to divide a gate signal-corresponding region of the corresponding gate signal by a unit gate shift amount in the rotating direction of the specimen analysis disc to define a plurality of divided regions, wherein the gate shift amount is equal to a positive integral multiple of the unit gate shift amount, generate positional information of the divided regions based on the measurement radial positional information and the count value of the corresponding gate signal to set count values of the divided regions.

According to a second aspect of the embodiments, there is provided an analysis method including: rotating a circular specimen analysis disc having a reaction region on which nanoparticles are captured; moving an optical pickup in a radial direction of the specimen analysis disc and detecting a measurement radial position for the optical pickup in the specimen analysis disc to generate measurement radial positional information; detecting a reference position defining portion formed in the specimen analysis disc to generate a reference position detection signal; irradiating the reaction region with laser light emitted from the optical pickup and receiving reflected light to generate a light reception detection signal; generating gate information including a gate shift amount based on the measurement radial positional information; generating a gate signal shifted by the gate shift amount in each measurement radial position in a rotating direction of the specimen analysis disc in accordance with the reference position detection signal and the gate information; extracting nanoparticle pulse signals generated every time the nanoparticle are scanned with the laser light from the light reception detection signal per gate signal, and counting the nanoparticle pulse signals to generate a count value of the corresponding gate signal; dividing gate signal-corresponding region of the corresponding gate signal by a unit gate shift amount in the rotating direction of the specimen analysis disc to define a plurality of divided regions, wherein the gate shift amount is equal to a positive integral multiple of the unit gate shift amount; and generating positional information the divided regions based on the measurement radial positional information and the count value of the corresponding gate signal to set count values in the divided regions.

DETAILED DESCRIPTION

First Embodiment

Figure 1:
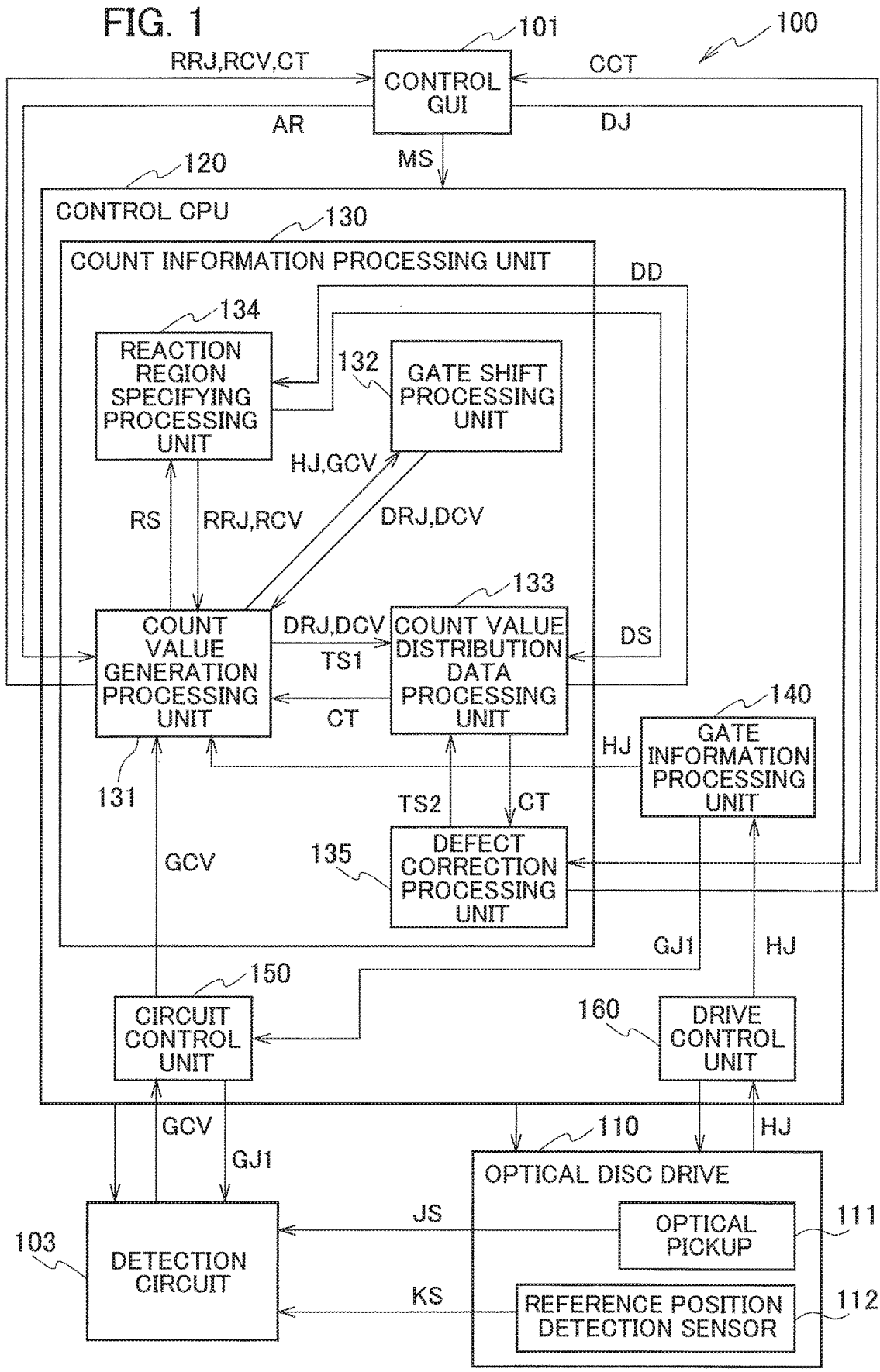
FIG. 1 is a configuration diagram showing an analysis device according to a first embodiment.

An analysis device according to a first embodiment is described below with reference to FIG. 1 to FIG. 8. As shown in FIG. 1, the analysis device 100 includes a control graphical user interface (GUI) 101, a control central processing unit (CPU) 120, a detection circuit 103, and an optical disc drive 110. The control GUI 101 receives an instruction by a user to output a startup command signal MS to the control CPU 120. The control CPU 120 starts up the detection circuit 103 and the optical disc drive 110 when the startup command signal MS is input.

The control CPU 120 includes a count information processing unit 130, a gate information processing unit 140, a circuit control unit 150, and a drive control unit 160. The count information processing unit 130 includes a count value generation processing unit 131, a gate shift processing unit 132, a count value distribution data processing unit 133, a reaction region specifying processing unit 134, and a defect correction processing unit 135. The count information processing unit 130, the gate information processing unit 140, the circuit control unit 150, and the drive control unit 160 may each be composed of software executed by the control CPU 120 or composed of hardware such as a circuit.

The count information processing unit 130 includes the count value generation processing unit 131, the gate shift processing unit 132, the count value distribution data processing unit 133, the reaction region specifying processing unit 134, and the defect correction processing unit 135. The count value generation processing unit 131, the gate shift processing unit 132, the count value distribution data processing unit 133, the reaction region specifying processing unit 134, and the defect correction processing unit 135 may each be composed of software executed by the control CPU 120 or composed of hardware such as a circuit. The optical disc drive 110 includes an optical pickup 111 and a reference position detection sensor 112.

Figure 2:
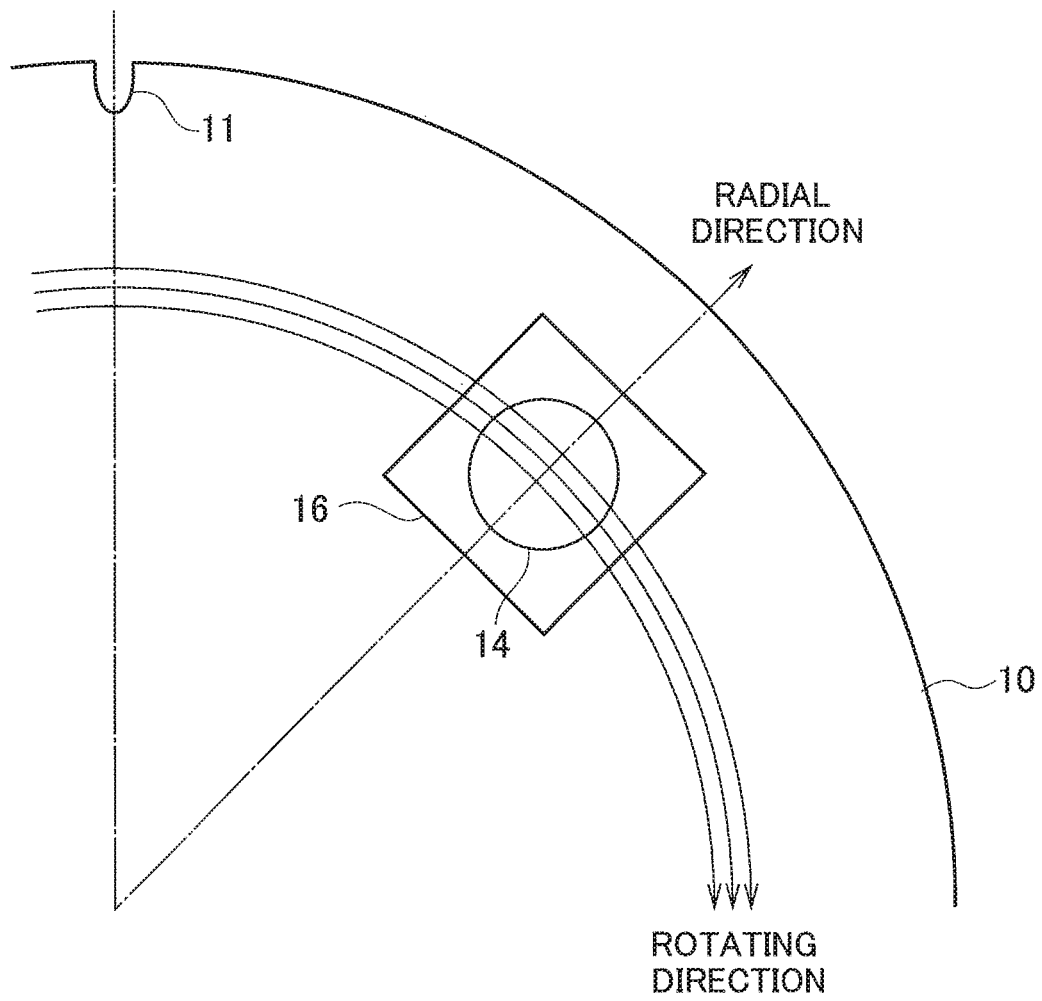
FIG. 2 is a plan view showing a part of a specimen analysis disc.

As shown in FIG. 2, the specimen analysis disc having a circular shape is provided with a reference position defining portion 11 which is a notch at the circumferential edge of the disc. The reference position defining portion 11 is used for defining a reference position in a rotating direction of the specimen analysis disc 10. The specimen analysis disc 10 is removably attached to the optical disc drive 110.

Figure 3:
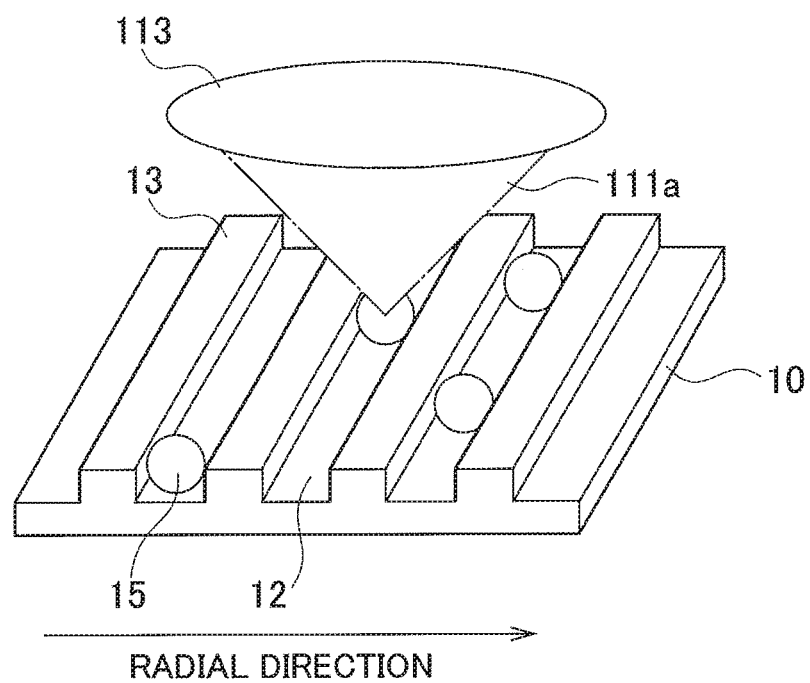
FIG. 3 is a perspective cross-sectional view schematically showing a state in which nanoparticles captured on a reaction region formed in the specimen analysis disc are detected by an optical pickup.

As shown in FIG. 3, the surface of the specimen analysis disc 10 is provided with recesses 12 and convex regions 13 alternately arranged in a radial direction. The recesses 12 and the convex regions 13 are formed in a spiral from the inner side to the outer side of the specimen analysis disc 10.

The recesses 12 correspond to grooves of an optical disc. The convex regions 13 correspond to lands of an optical disc. A track pitch of the specimen analysis disc 10, which corresponds to a track pitch of an optical disc, is 320 nanometers, for example. As shown in FIG. 2 and FIG. 3, nanoparticles 15 specifically binding to detection target substances by an antigen-antibody reaction are captured on the recesses 12 in a reaction region 14 formed on the specimen analysis disc 10.

Returning to FIG. 1, the drive control unit 160 controls the optical disc drive 110. For example, the drive control unit 160 drives or stops the optical disc drive 110. The optical disc drive 110 controls the specimen analysis disc 10 to rotate or stop. The optical disc drive 110 moves the optical pickup 111 in the radial direction of the specimen analysis disc 10 to a target measurement radial position.

As shown in FIG. 3, the optical pickup 111 includes an objective lens 113. The optical disc drive 110 moves the optical pickup 111 to the measurement radial position at which the measurement of the specimen analysis disc 10 starts, and causes the optical pickup 111 to emit laser light 111*a* toward the specimen analysis disc 10.

The optical disc drive 110 can adjust the objective lens 113 in a vertical direction so that the laser light 111*a* is condensed on the recess 12 in the reaction region 14. The reaction region 14 is irradiated with the laser light 111*a* emitted from the optical pickup 111 with the specimen analysis disc 10 rotating so as to be scanned along the recess 12 corresponding to a track of the specimen analysis disc 10.

The optical pickup 111 receives the reflected light of the laser light 111*a* from the specimen analysis disc 10 to generate a light reception detection signal JS, and outputs the signal to the detection circuit 103. The optical disc drive 110 detects the measurement radial position for the optical pickup 111 in the specimen analysis disc 10 to generate measurement radial positional information HJ, and outputs the information to the drive control unit 160. The drive control unit 160 outputs the measurement radial positional information HJ to the gate information processing unit 140. The gate information processing unit 140 outputs the measurement radial positional information HJ to the count value generation processing unit 131.

The reference position detection sensor 112 is placed adjacent to the circumferential edge of the specimen analysis disc 10. The reference position detection sensor 112 is an optical sensor such as a photodetector. The reference position detection sensor 112 detects the reference position defining portion 11 in the specimen analysis disc 10 to generate a reference position detection signal KS, and outputs the signal to the detection circuit 130.

The gate information processing unit 140 generates gate information GJ1 including a reference shift amount φa, phase difference φa+Δφa, and a gate width W based on the measurement radial positional information HJ, and outputs the information to the circuit control unit 150. The reference shift amount aφ, the phase difference φa+Δφa, and the gate width W will be described below. The circuit control unit 150 outputs the gate information GJ1 to the detection circuit 103.

Figure 4:
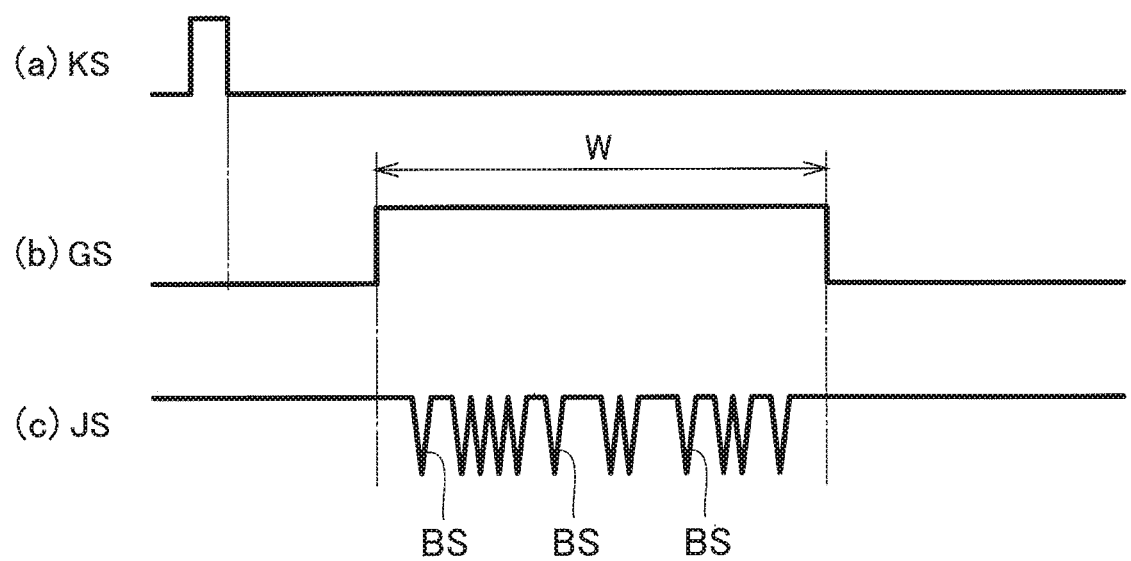
FIG. 4 is a view showing a relationship between a reference position detection signal, agate signal, and a light reception detection signal.

The detection circuit 103 generates a gate signal GS based on the gate information GJ1. The detection circuit 103 synchronizes the timing between the gate signal GS and the light reception detection signal JS on the basis of the reference position detection signal KS, as shown in FIG. 4. A method of generating gate signals GS will be described below.

The detection circuit 103 extracts nanoparticle pulse signals BS from the light reception detection signal JS per gate signal GS. The nanoparticle pulse signals BS are generated every time the nanoparticles are scanned with the laser light 111*a*. The detection circuit 103 counts the extracted nanoparticle pulse signals BS, generates count values GCV (first count values) of the corresponding gate signals GS, and sequentially outputs the values to the circuit control unit 150 per gate signal GS. The circuit control unit 150 sequentially outputs the count values GCV of the corresponding gate signals GS to the count value generation processing unit 131 per gate signal GS.

The method of generating the gate signals GS is described below with reference to FIG. 5A, FIG. 5B, FIG. 5C, FIG. 6A, and FIG. 6B. The gate information processing unit 140 sets the gate width W of each gate signal GS in each measurement radial position (track) of the specimen analysis disc 10 so as to divide a measurement region 16 including the reaction region 14 shown in FIG. 2 into the number m (m is an integer of two or more) in the rotating direction of the specimen lysis disc 10. The gate width W is determined according to the rotation number of the specimen analysis disc 10 in the respective measurement radial positions. When the specimen analysis disc 10 is rotated at a constant linear velocity, the gate widths W in the respective measurement radial positions are set to be the same.

Figure 5A:
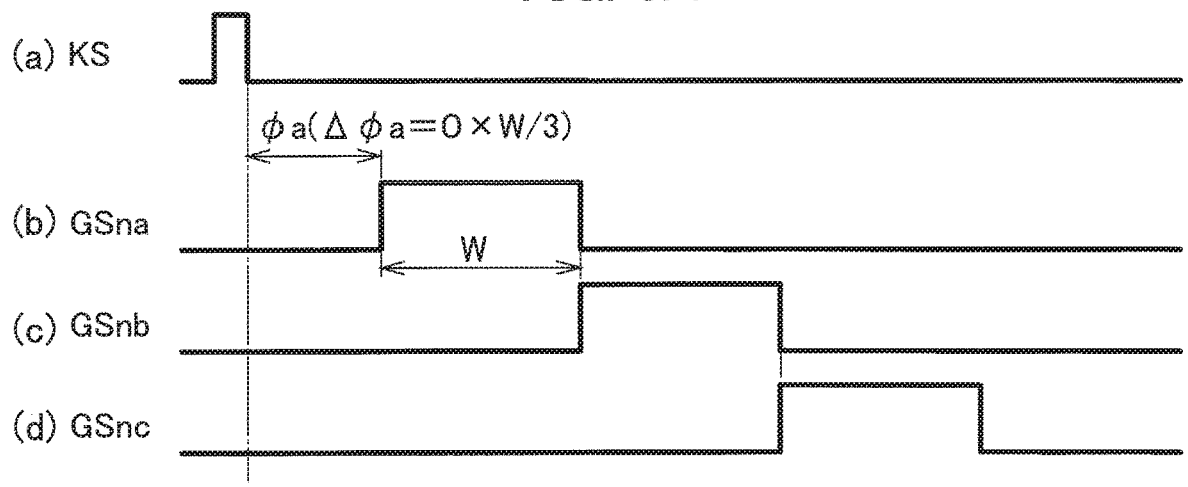
FIG. 5A is a view showing a relationship between the reference position detection signal and gate signals.

A case of setting the gate width W of each gate signal GS to divide the measurement region 16 into three (m=3) is described below with reference to FIG. 5A to FIG. 5C. The gate information processing unit 140 sets the gate width W of each gate signal GS so as to divide the measurement region 16 into three in the rotating direction of the specimen analysis disc 10.

The gate information unit 140 sets the reference shift amount φa for each measurement radial position. The gate information processing unit 140 sets, as the reference shift amount φa, period of time from a point at which the reference position defining portion 11 is detected to a point at which the measurement region 16 reaches a measurement radial position rn corresponding to a track TRn (n is the track number) on the basis of the reference position detection signal KS, as shown in FIG. 5A. For example, the gate information processing unit 140 sets, as the reference shift amount φa, the period of time from the fall of the reference position detection signal KS to the rise of the first gate signal GSn.

The gate information processing unit 140 sets a unit gate shift amount Δφua (Δφua=W/m, m=3 in this embodiment) so as to divide the gate width W into three. The gate information processing unit 140 further sets a gate shift amount Δφa to 0×Δφua (=0×W/3) in the measurement radial position rn. Namely, the gate information processing unit 140 sets the gate shift amount Δφa to 0 and sets the phase difference to φa in the measurement radial position rn.

Figure 5B:
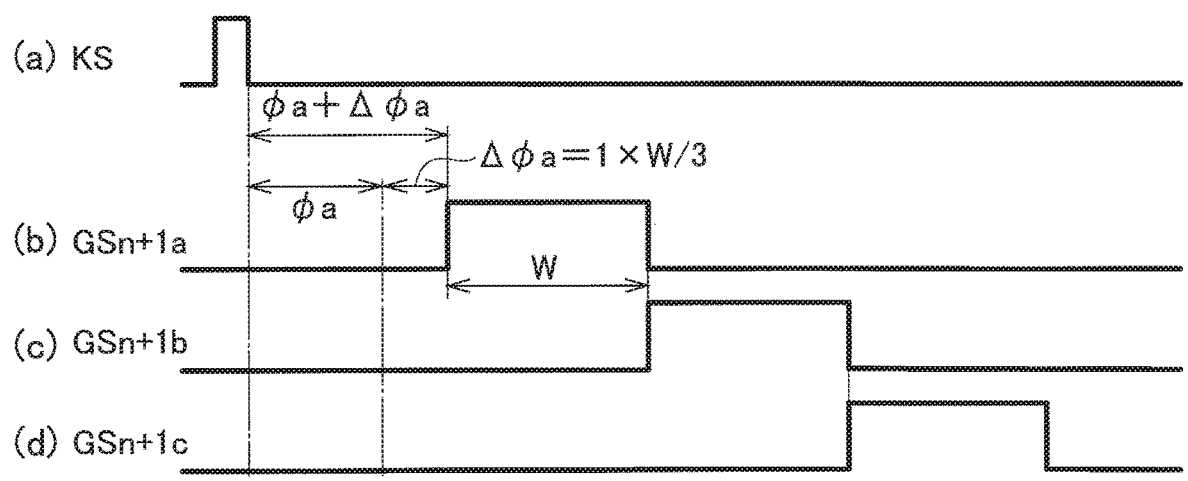
FIG. 5B is a view showing a relationship between the reference position detection signal and gate signals.

The gate information processing unit 140 sets the gate shift amount Δφa to 1×Δφua (=1×W/3) in a measurement radial position rn+1 corresponding to a track TRn+1 next to the track TRn, as shown in FIG. 5B. Namely, the gate information processing unit 140 sets the gate shift amount Δφa to W/3 and sets the phase difference to φa+W/3 in the measurement radial position rn+1.

Figure 5C:
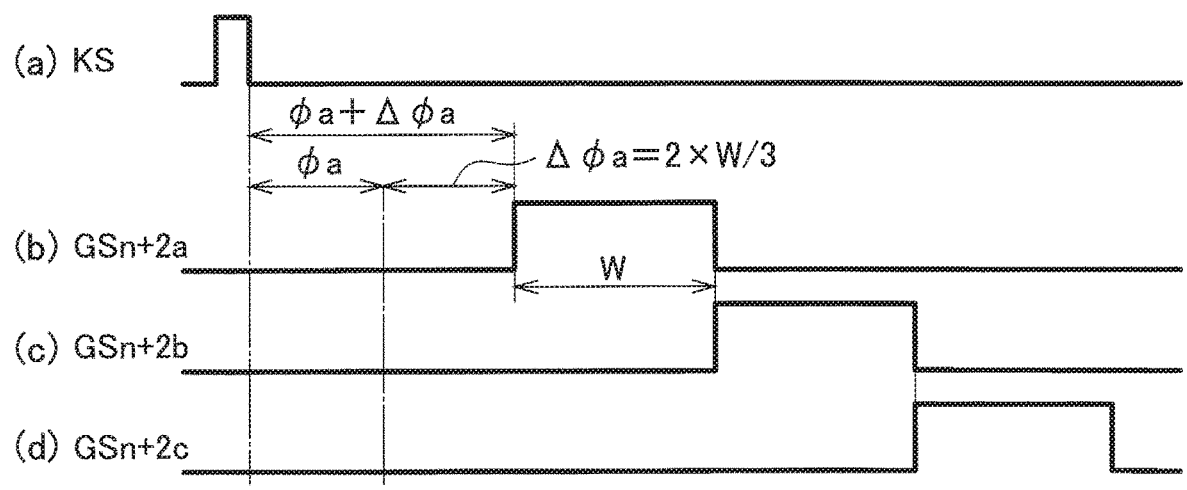
FIG. 5C is a view showing a relationship between the reference position detection signal and gate signals.

The gate information processing unit 140 sets the gate shift amount Δφa to 2×Δφa (=2×W/3) in a measurement radial position rn+2 corresponding to a track TRn+2 next to the track TRn+1, as shown in FIG. 5C. Namely, the gate information processing unit 140 sets the gate shift amount Δφa to 2×W/3 and sets the phase difference to φa+2×W/3 in the measurement radial position rn+2.

The gate shift amount Δφa is equal to a positive integral multiple of the unit gate shift amount Δφua.

The detection circuit 103 generates the gate signals GS based on the reference position detection signal KS and the gate information GJ1. For example, the detection circuit 103 generates a gate signal GSna which raises after the fall of the reference position detection signal KS with the phase difference φa in the measurement radial position rn, and sequentially generates a gate signal GSnb and a gate signal GSnc.

The detection circuit 103 generates a gate signal GSn+1a which raises after the fall of the reference position detection signal KS with the phase difference φa+W/3 in the measurement radial position rn+1, and sequentially generates a gate signal GSn+1b and a gate signal GSn+1c. The detection circuit 103 further generates a gate signal GSn+2a which raises after the fall of the reference position detection signal KS with the phase difference φa+2×W/3 in the measurement radial position rn+2, and sequentially generates a gate signal GSn+2b and a gate signal GSn+2c.

In other words, the gate signal GSn+1a is generated with a delay of Δφa=W/3 from the gate signal GSna. The gate signal GSn+2a is generated with a delay of Δφa=2×W/3 from the gate signal GSna. Similarly, the gate signal GSn+1b and the gate signal. GSn+2b are generated with a delay of the gate shift amount Δφa=W/3 and a delay of the gate shift amount Δφa=2×W/3, respectively, from the gate signal GSnb. The gate signal GSn+1c and the gate signal GSn+2c are generated with a delay of the gate shift amount Δφa=W/3 and a delay of the gate shift amount Δφa=2×W/3, respectively, from the gate signal GSnc.

Figure 6A:
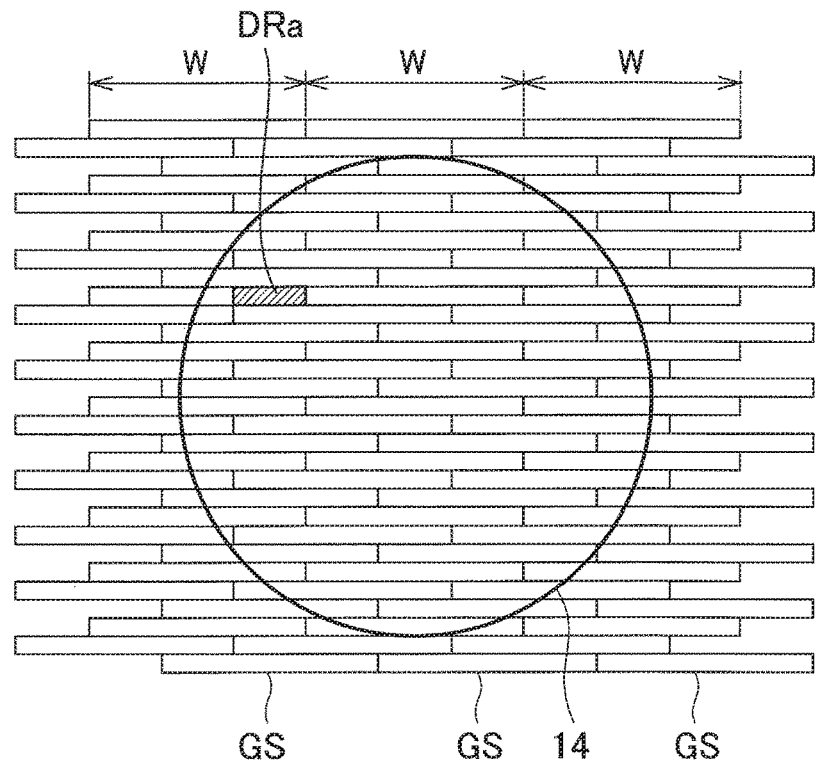
FIG. 6A is a view showing a state in which gate signals are shifted in the respective measurement radial positions in a rotating direction of the specimen analysis disc.
Figure 6B:
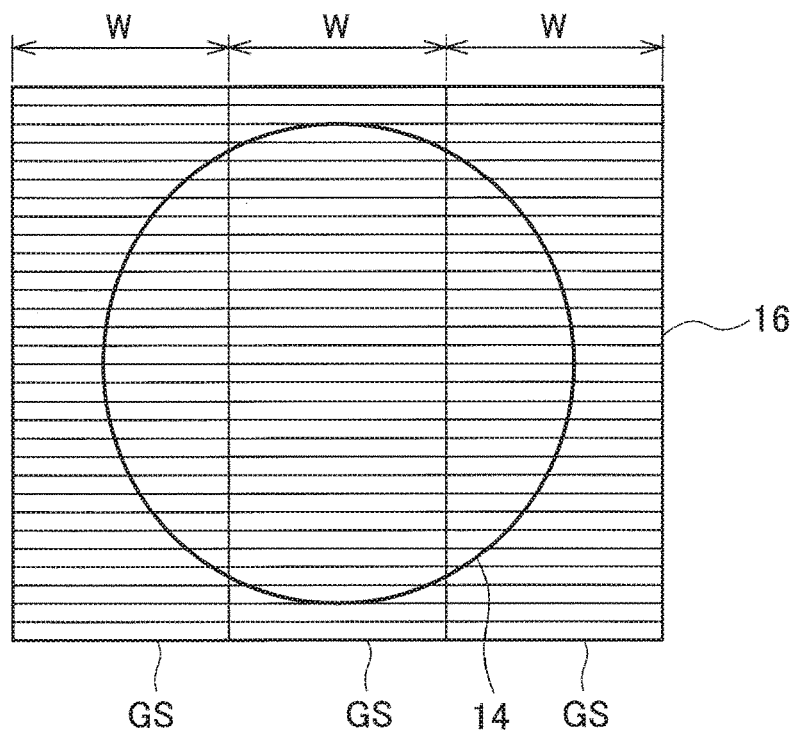
FIG. 6B is a view showing a state in which gate signals are not shifted in the respective measurement radial positions in the rotating direction of the specimen analysis disc.

The detection circuit 103 repeatedly executes the same processing in the respective measurement radial positions of the corresponding tracks TR in the radial direction of the specimen analysis disc 10 as in the measurement radial positions rn, rn+1, and rn+2. Accordingly, the gate signals GS shifted in the respective measurement radial positions in the rotating direction of the specimen analysis disc 10 are generated, as shown in FIG. 6A. FIG. 6B illustrates gate signals GS of a comparative example not shifted in the respective measurement radial positions in the rotating direction of the specimen analysis disc 10.

The detection circuit 103 sequentially outputs the count values GCV of the corresponding gate signals GS shown in FIG. 6A to the count value generation processing unit 131 via the circuit control unit 150 per gate signal GS. The count value generation processing unit 131 outputs the measurement radial positional information HJ to the gate shift processing unit 132, and sequentially outputs the count values GCV of the corresponding gate signals GS to the gate shift processing unit 132 per gate signal GS.

Figure 7A:
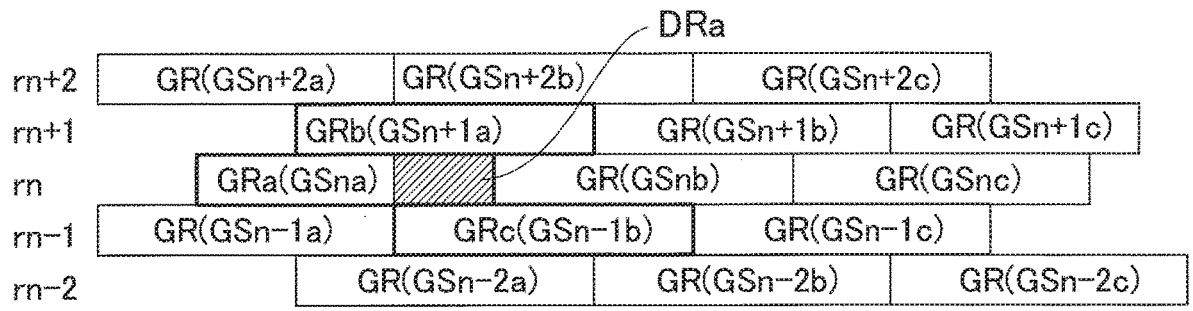
FIG. 7A is a view showing a relationship between divided regions in the reaction region divided by a unit gate shift amount in the rotating direction of the specimen analysis disc and measurement gate signal-corresponding regions corresponding to the respective gate signals.
Figure 7B:
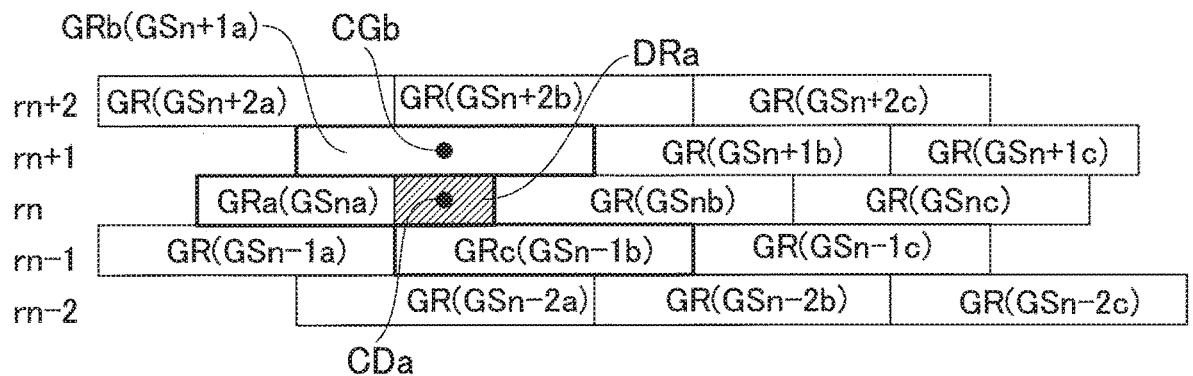
FIG. 7B is a view showing a relationship between the divided regions in the reaction region divided by the unit gate shift amount in the rotating the specimen analysis disc and the measurement gate signal-corresponding regions corresponding to the respective gate signals.
Figure 7C:
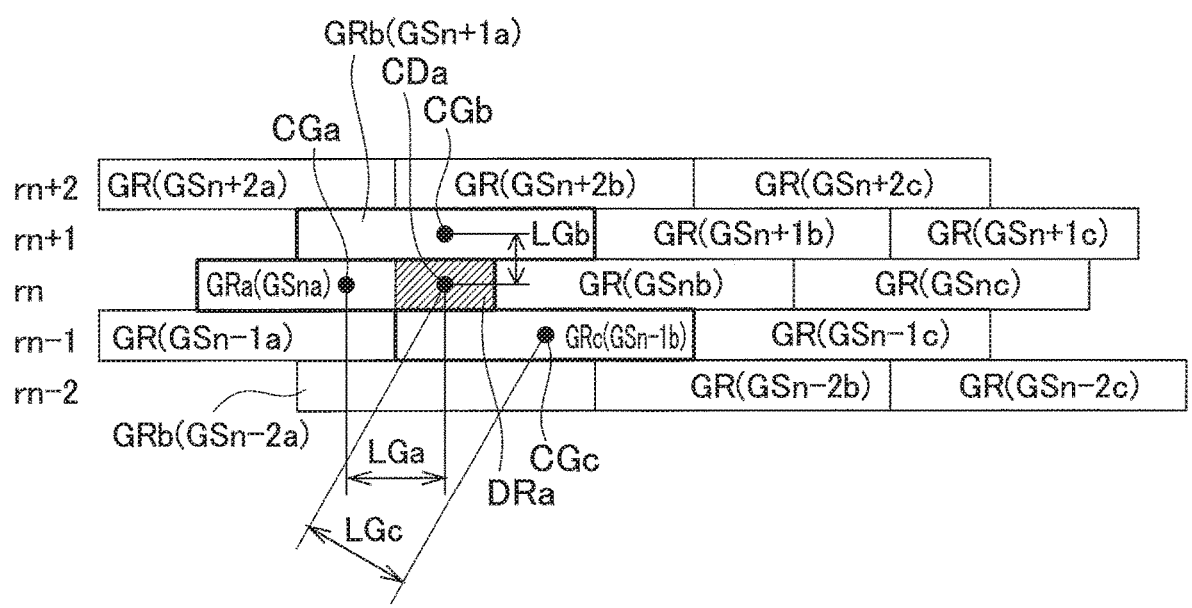
FIG. 7C is a view showing a relationship between the divided regions in the reaction region divided by the unit gate shift amount in the rotating direction of the specimen analysis disc and the measurement gate signal-corresponding regions corresponding to the respective gate signals.

A method for improving the measurement resolution in the rotating direction of the specimen analysis disc 10 is described below with reference to FIG. 7A, FIG. 7B, FIG. 7C, and FIG. 8. FIG. 7A to FIG. 7C show relationship between gate signal-corresponding regions corresponding to the respective gate signals GS and divided regions in the reaction region 14 divided by the unit gate shift amount Δφua (Δφua=W/3) in the rotating direction of the specimen analysis disc 10. The signs GR shown in FIG. 7A to FIG. 7C denote the gate signal-corresponding regions of the corresponding gate signals GS. The gate signal-corresponding regions GR are regions in the specimen analysis disc 10 defined when the corresponding gate signals GS are measured.

The gate shift processing unit 132 divides each gate signal-corresponding region GR by the unit gate shift amount Δφua (Δφua=W/3) in the rotating direction of the specimen analysis disc 10 in each measurement radial position, so as to define a plurality of divided regions DR. The divided regions DRa shown in FIG. 7A to FIG. 7C and FIG. 8 correspond to the divided region DRa shown in FIG. 6A. The divided region DRa is included in a gate signal-corresponding region GRa corresponding to the gate signal GSna, and a width of the divided region DRa in the rotating direction of the specimen analysis disc 10 is a third of the width of the gate signal-corresponding region GRa. The gate shift processing unit 132 sets count values DCV (second count values) in the respective divided regions DR in accordance with the measurement radial positional information HJ and the count values GCV corresponding to the respective gate signals GS.

A first setting method of setting the count values DCV in the divided regions DR is described with reference to FIG. 7A. The gate shift processing unit 132 calculates an average value of a count value GCVna of the gate signal GSna corresponding to the gate signal-corresponding region GRa, a count value GCVn+1a of the gate signal. GSn+1a corresponding to a gate signal-corresponding region GRb adjacent to one side of the divided region DRa in the radial direction of the specimen analysis disc 10, and a count value GCVn−1b of a gate signal GSn−1b corresponding to a gate signal-corresponding region GRc adjacent to the other side of the divided region DRa, or calculates a value obtained by multiplying the average by a third, so as to set the obtained value as a count value DCVa in the divided region DRa. The gate shift processing unit 132 sets the count values DCV in the other divided regions DR in the same manner as in the divided region DRa.

A second setting method of setting the count values DCV in the divided regions DR is described with reference to FIG. 7B. The gate shift processing unit 132 compares distances between a central point CDa of the divided region DRa and the respective central points CG of the gate signal-corresponding regions GR around the divided region DRa. The gate shift processing unit 132 specifies the gate signal-corresponding region GRb having a central point CGb with the shortest distance from the central point CDa of the divided region DRa in accordance with the comparison result.

The gate shift processing unit 132 sets, as the count value DCVa in the divided region DRa, the count value of the gate signal GSn+1a corresponding to the gate signal-corresponding region GRb or a value obtained by multiplying the count value by a third. The gate shift processing unit 132 sets the count values DCV in the other divided regions DR in the same manner as in the divided region DRa.

A third setting method of setting the count values DCV in the divided regions DR is described with reference to FIG. 7C. A distance between the central point CDa of the divided region DRa and a central point CGa of the gate signal-corresponding region GRa is set s a first distance LGa. A distance between the central point CDa of the divided region DRa and a central point CGb of the gate signal-corresponding region GRb is set as a second distance LGb. A distance between the central point CDa of the divided region DRa and a central point CGc of the gate signal-corresponding region GRc is set as a third distance LGc. The gate shift processing unit 132 compares the first distance LGa, the second distance LGb, and the third distance LGc.

The first distance LGa is W/3. When a distance between the divided regions DR in the radial direction of the specimen analysis disc 10 is set as LP, the second distance LGb is LP. The third distance LGc is $[LP^2+(W/3)^2]^{1/2}$. The first, second, and third distances LGa, LGb, and LGc, have a relationship of LGb<LGa<LGc. The gate shift processing unit 132 executes weighting processing of the count values of the gate signals GSna, GSn+1a, and GSn−1b corresponding to the gate signal-corresponding regions GRa, GRb, and GRc in accordance with the first, second, and third distances LGa, LGb, and LGc, so as to set the count value DCVa for the divided region DRa.

For example, the gate shift processing unit 132 multiplies the count value of the gate signal GSn+1a corresponding to the gate signal-corresponding region GRb having the second distance LGb by a second weighting coefficient αb. The gate shift processing unit 132 multiplies the count value of the gate signal GSn−1b corresponding to the gate signal-corresponding region GRc having the third distance LGc by a third weighting coefficient αc (αb>αc). The gate shift processing unit 132 multiplies the count value of the gate signal GSna corresponding to the gate signal-corresponding region GRa having the first distance LGa by a first weighting coefficient αa (αb>αa>αc).

The gate shift processing unit 132 adds up the products of the count values multi led by the respective weighting coefficients αa, αb, and αc, and sets the obtained value as the count value DCVa in the divided region DRa. The gate shift processing unit 132 sets the count values DCV in the other divided regions DR in the same manner as in the divided region DRa.

Figure 8:
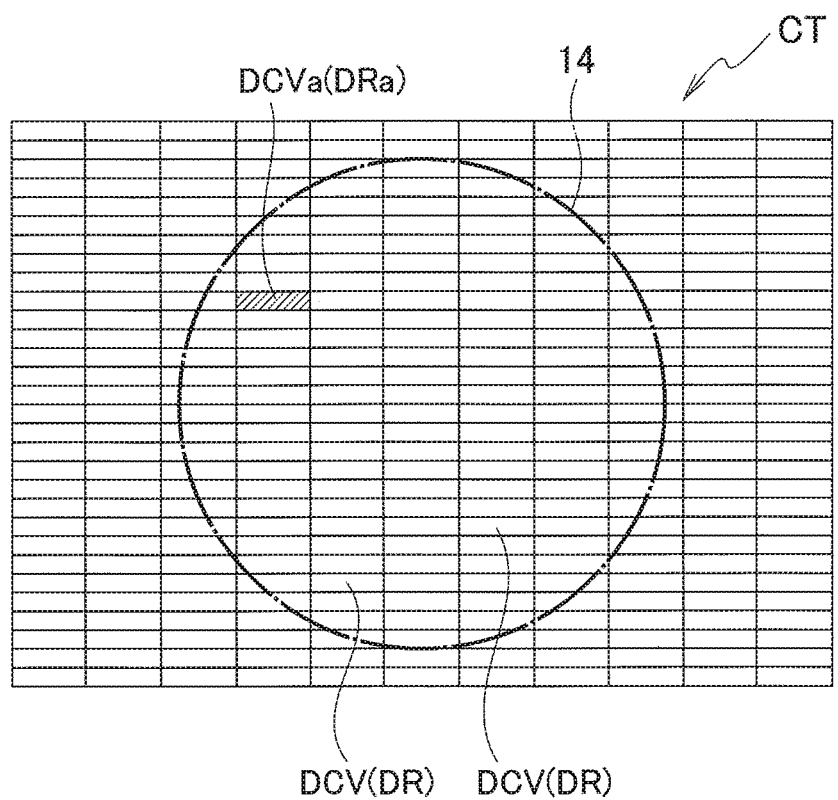
FIG. 8 is a view showing a relationship between the reaction region and the divided regions.

The gate shift processing unit 132 generates positional information (for example, central position coordinate information) DRJ of the respective divided regions DR, and outputs the positional information DRJ of the respective divided regions DR and the count values DCV in the respective divided regions DR to the count value generation unit 131. The count value generation unit 131 outputs the positional information DRJ of the respective divided regions DR and the count values DCV in the respective divided regions DR to the count value distribution data processing unit 133. The count value distribution data processing unit 133 stores the count values DCV of the respective divided regions DR in a count value distribution data table CT in accordance with the positional information DRJ of the respective divided regions DR, as shown in FIG. 8.

The count value generation processing unit 131 determines whether the measurement of the reaction region 14 is completed according to the measurement radial positional information HJ. When the measurement is determined to be completed, the count value generation processing unit 131 generates a reaction region specifying signal RS and outputs the signal to the reaction region specifying processing unit 134.

The reaction region specifying processing unit 134 generates a distribution data acquisition signal DS based on the reaction region specifying signal RS, and outputs the signal to the count value distribution data processing unit 133. The count value distribution data processing unit 133 outputs, to the reaction region specifying processing unit 134, the count values DCV in respective divided regions DR stored in the count value distribution data table CT as count value distribution data DD in accordance with the distribution data acquisition signal DS.

Figure 9A:
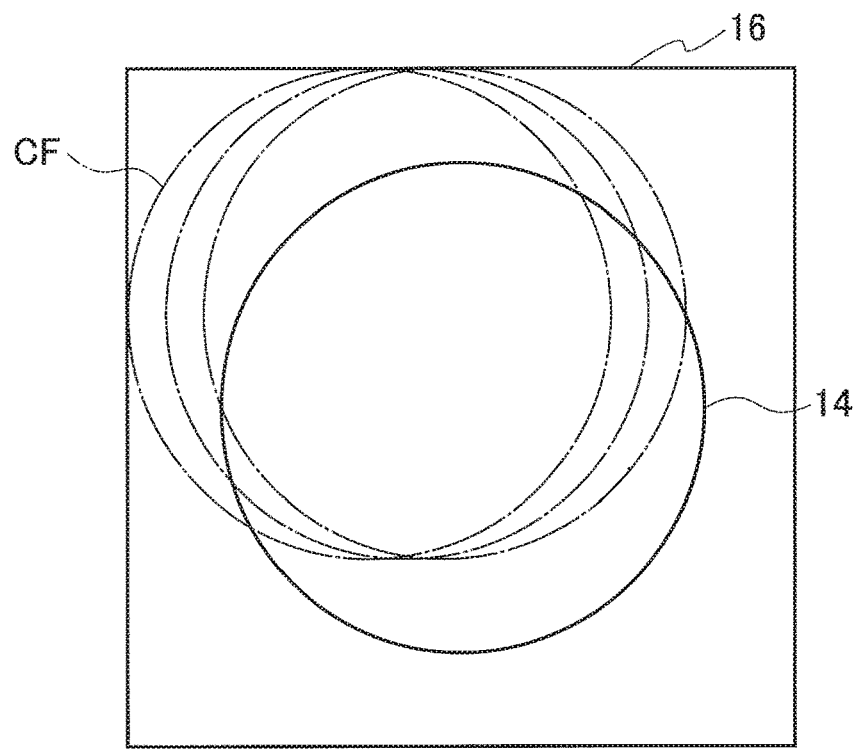
FIG. 9A is a view showing a relationship between the reaction region and filters in a measurement region.
Figure 9B:
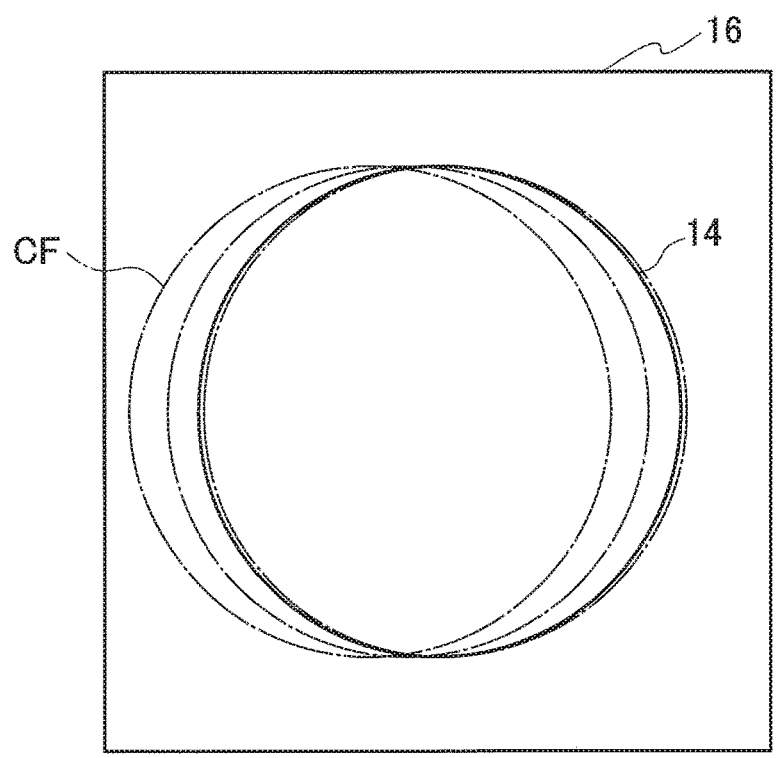
FIG. 9B is a view showing a relationship between the reaction region and filters in the measurement region.

The reaction region specifying processing unit 134 specifies the position of the reaction region 14 in accordance with the count value distribution data DD (the count values DCV in respective divided regions DR), and determines a count value RCV in the reaction region 14. For example, as shown in FIG. 9A and FIG. 9B, the reaction region specifying processing unit 134 scans the entire measurement region 16 with a filter CF having the same design in shape as the reaction region 14, and determines a position where the filter CF has the largest count value.

The reaction region specifying processing unit 134 specifies the position of the reaction region 14 (for example, a central position coordinate) in accordance with the termination result to generate positional information RRJ of the reaction region 14, and determines the count value RCV in the reaction region 14 based on the count value distribution data DD. The count value RCV in the reaction region 14 corresponds to the number of nanoparticles 15 captured in the reaction region 14 and the number of detection target substances specifically bound to the nanoparticles 15.

When the reaction region 14 is formed into a circular shape, the filter CF has the same circular shape as the reaction region 14. Any other method that can specify the position of the reaction region 14 may be used instead. The reaction region specifying processing unit 134 outputs the positional information RRJ of the reaction region 14 and the count value RCV in the reaction region 14 to the count value generation processing unit 131.

When the measurement is determined to be completed, the count value generation processing unit 131 generates a distribution data table acquisition signal TS1 and outputs the signal to the count value distribution data processing unit 133. The count value distribution data processing unit 133 outputs the count value distribution data table CT to the count value generation processing unit 131 when the distribution data table acquisition signal TS1 is input.

When an acquisition request AR for the measurement result is made by the control GUI 101, the count value generation processing unit 131 outputs, to the control GUI 101, the positional information RRJ of the reaction region 14, the count value RCV in the reaction region 14, and the count value distribution data table CT. The control GUI 101 displays a count value distribution of the reaction region 14 obtained by associating the reaction region 14 with the count value distribution data table CT or displays the count value RCV of the reaction region 14.

The user observes the count value distribution of the reaction region 14, and determines whether a defect region is present in the reaction region 14. The defect region is a region in which no nanoparticle is captured because bubbles in a solution adhere to the reaction region 14 during the process of forming the reaction region 14. When the defect region is determined to be present, the user specifies a range of the defect region. The control GUI 101 outputs defect region information DJ including the specified defect region to the defect correction processing unit 135.

The defect correction processing unit 135 generates a distribution data table acquisition signal TS2 when the defect region information DJ is input, and outputs the signal to the count value distribution data processing unit 133. The count value distribution data processing unit 133 outputs the count value distribution data table CT to the defect correction processing unit 135 when the distribution data table acquisition signal TS2 is input.

The defect correction processing unit 135 specifies the defect region in the count value distribution data table CT according to the defect region information DJ, and determines that the other region not specified as the defect region is a normal measurement region. The defect correction processing unit 135 corrects the count value of the defect region in the count value distribution data table CT based on the count value in the normal measurement region, and generates a corrected count value distribution data table CCT.

The defect correction processing unit 135 outputs the corrected count value distribution data table CCT to the control GUI 101. The control GUI 101 displays the corrected count value distribution data table CCT. The defect correction processing unit 135 may output the corrected count value distribution data table CCT to the count value generation processing unit 131, and the count value generation processing unit 131 may then output the corrected count value distribution data table CCT to the control GUI 101.

Figure 10A:
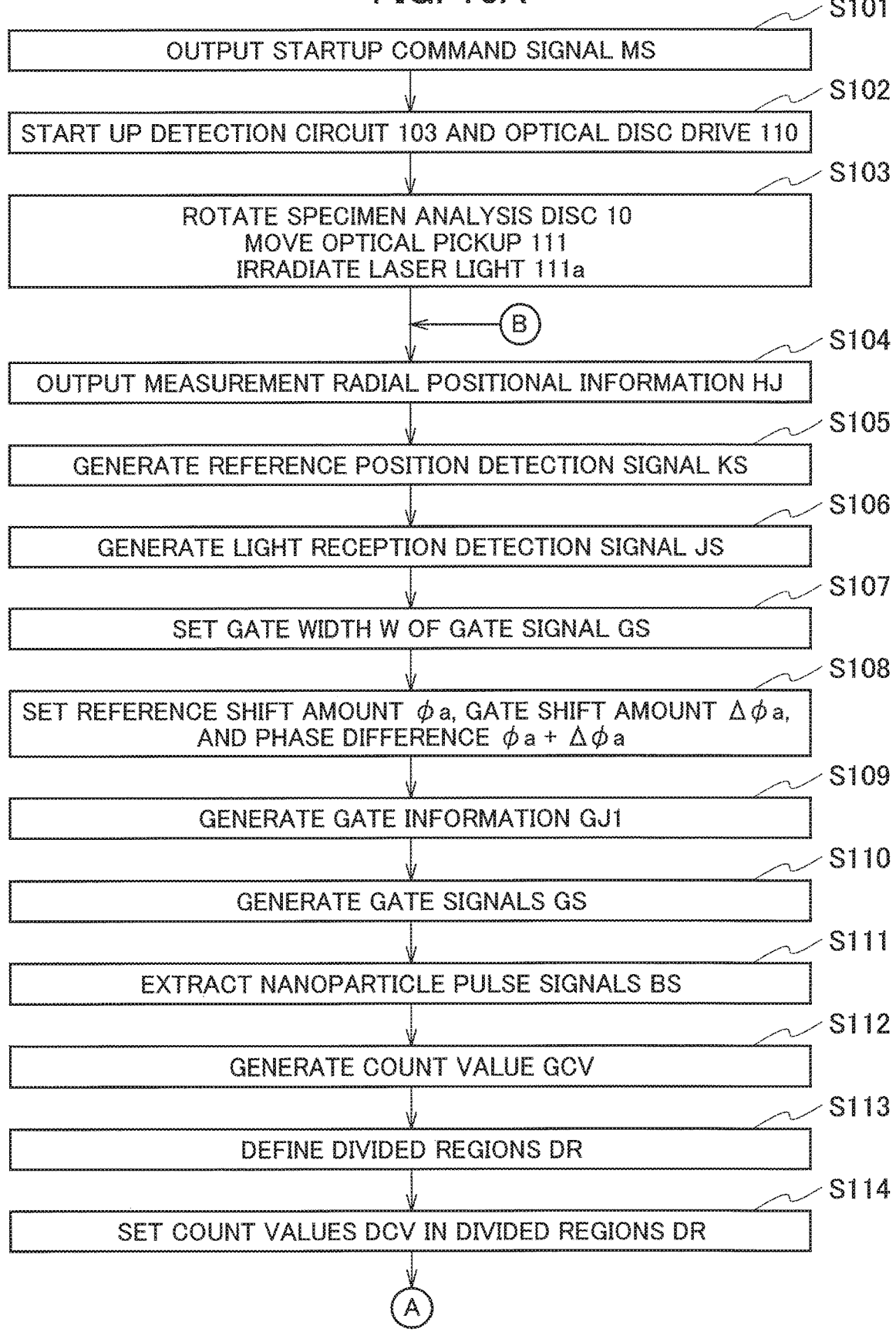
FIG. 10A is a flowchart showing an analysis method of analyzing nanoparticles in the reaction region by the analysis device according to the first embodiment.
Figure 10B:
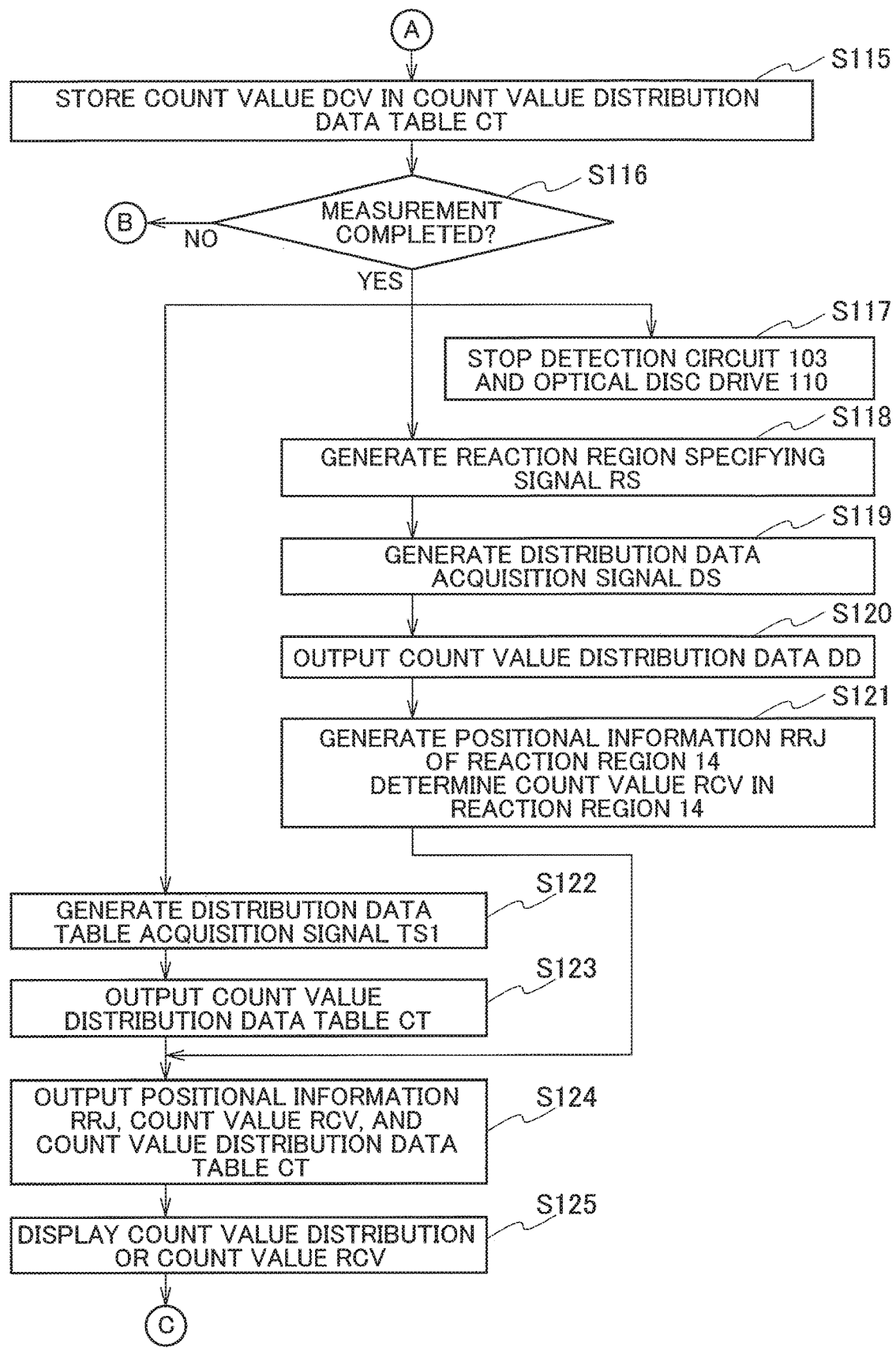
FIG. 10B is a flowchart showing the analysis method of analyzing nanoparticles in the reaction region by the analysis device according to the first embodiment.

An analysis method by the analysis device 100 according to the first embodiment is described below with reference to the flowcharts shown in FIG. 10A, FIG. 10B, and FIG. 10C. In step S101 shown in FIG. 10A, the control GUI 101 outputs the startup command signal MS to the control CPU 120 in accordance with the instruction by the user. When the startup command signal MS is input, the control CPU 120 starts up the detection circuit 103 and the optical disc drive 110 in step S102.

In step S103, the drive control unit 160 of the control CPU 120 controls the optical disc drive 110 to control the rotation of the specimen analysis disc 10. The drive control unit 160 of the control CPU 120 further controls the optical disc drive 110 to move the optical pickup 111 to the target measurement radial position in the specimen analysis disc 10 and direct the optical pickup 111 to emit the laser light 111a to the specimen analysis disc 10.

In step S104, the optical disc drive 110 detects the measurement radial position for the optical pickup 111 in the specimen analysis disc 10 to generate the measurement radial positional information HJ, and outputs the information to the count value generation processing unit 131 via the drive control unit 160 and the gate information processing unit 140. In step S105, the reference position detection sensor 112 detects the reference position defining portion 11 in the specimen analysis disc 10 and generates the reference position detection signal KS. In step S106, the optical pickup 111 receives the reflected light from the specimen analysis disc 10 and generates the light reception detection signal JS.

In step S107, the gate information processing unit 140 sets the gate width W of each gate signal GS in each measurement radial position so as to divide the measurement region 16 into the number m in the rotating direction of the specimen analysis disc 10. The optical disc drive 110 and the gate information processing unit 140 may execute the steps S104 to S106 and step S107 simultaneously.

In step S108, the gate information processing unit 140 sets, as the reference shift amount φa, the period of time from the point at which the reference position defining portion 11 is detected to the point at which the measurement region 16 reaches the measurement radial position, in accordance with the measurement radial positional information HJ. The gate information processing unit 140 sets the gate shift amount Δφa and the phase difference φa+Δφa for each measurement radial position (track).

In step S109, the gate information processing unit 140 generates the gate information GJ1 based on the measurement radial positional information HJ, and outputs the information to the detection circuit 103 via the circuit control unit 150. In step S110, the detection circuit 103 generates the gate signals GS shifted in the respective measurement radial positions in the rotating direction of the specimen analysis disc 10 on the basis of the reference position detection signal KS and the gate information GJ1.

In step S111, the detection circuit 103 extracts the nanoparticle pulse signals BS from the light reception detection signal JS per gate signal GS. In step S112, the detection circuit 103 counts the extracted nanoparticle pulse signals BS and generates the count value GCV of the corresponding gate signal GS. The detection circuit 103 then sequentially outputs the count values GCV per gate signal GS to the count value generation processing unit 131 via the circuit control unit 150.

In step S113, the gate shift processing unit 132 divides the reaction region 14 by the unit gate shift amount Δφua in each measurement radial position in the rotating direction of the specimen analysis disc 10 so as to define a plurality of divided regions DR. In step S114, the gate shift processing unit 132 sets the count values DCV of the divided regions DR in accordance with the count value in the gate signal-corresponding region GR including the divided regions DR and the count values in the gate signals GS corresponding to the peripheral gate signal-corresponding regions around the divided regions DR. The gate shift processing unit 132 further outputs the positional information DRJ of the respective divided regions DR and the count values DCV in the divided regions DR to the count value distribution data processing unit 133 via the count value generation processing unit 131.

In step S115 shown in FIG. 10D, the count value distribution data processing unit 133 stores the count values DCV of the respective divided regions DR in the count value distribution data tale CT in accordance with the positional information DRJ of the respective divided regions DR and the count values DCV in the respective divided regions DR.

In step S116, the count value generation processing unit 131 determines whether the measurement of the reaction region 14 is completed according to the measurement radial positional information HJ. When the measurement is determined not to be completed yet (NO in step S116), the control CPU 120 causes the process to return to step S104. When the measurement is determined to be completed (YES in step S116), the control CPU 120 stops the detection circuit 103 and the optical disc drive 110 in step S117.

When the measurement is determined to be completed in step S116, the count value generation processing unit 131 generates the reaction region specifying signal RS and outputs the signal to the reaction region specifying processing unit 134 in step S118. When the reaction region specifying signal RS is input, the reaction region specifying processing unit 134 generates the distribution data acquisition signal DS and outputs the signal to the count value distribution data processing unit 133 in step S119. When the distribution data acquisition signal DS is input, the count value distribution data processing unit 133 outputs, to the reaction region specifying processing unit 134, the count values DCV in the respective divided regions DR stored in the count value distribution data table CT as count value distribution data DD in step S120.

In step S121, the reaction region specifying processing unit 134 scans the entire measurement region 16 with the filter CF having the same shape as the reaction region 14, and determines a position where that filter FC has the largest count value. The reaction region specifying processing unit 134 specifies the position of the reaction region 14 (for example, the central position coordinate) in accordance with the determination result to generate the positional information RRJ of the reaction region 14, and determines the count value RCV in the reaction region 14. The reaction region specifying processing unit 134 outputs the positional information RRJ of the reaction region 14 and the count value RCV in the reaction region 14 to the count value generation processing unit 131.

When the measurement is determined to be completed in step S116, the count value generation processing unit 131 generates the distribution data table acquisition signal TS1 and outputs the signal to the count value distribution data processing unit 133 in step S122. When the distribution data table acquisition signal TS1 is input, the count value distribution data processing unit 133 outputs the count value distribution data table CT to the count value generation processing unit 131 in step S123.

When the acquisition request AR for the measurement result is made by the control GUI 101, the count value generation processing unit 131 outputs, to the control GUI 101, the positional information RRJ of the reaction region 14, the count value RCV in the reaction region 14, and the count value distribution data table CT in step S124. In step S125, the control GUI 101 displays the count value distribution of the reaction region 14 obtained by associating the reaction region 14 with the count value distribution data table CT or displays the count value RCV of the reaction region 14.

Figure 10C:
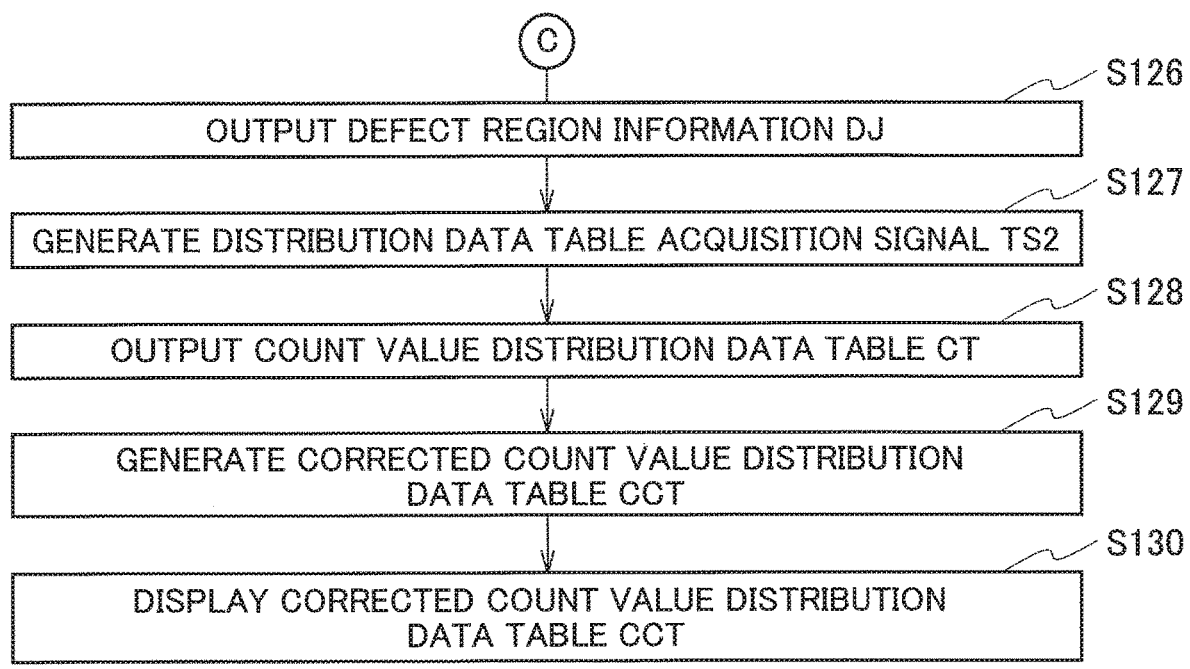
FIG. 10C is a flowchart showing the analysis method of analyzing nanoparticles in the reaction region by the analysis device according to the first embodiment.

When the user specifies a range of a defect region, the control GUI 101 outputs the defect region information DJ including the specified defect region to the defect correction processing unit 135 in step S126 shown in FIG. 10C. The defect correction processing unit 135 generates the distribution data table acquisition signal TS2 when the defect region information DJ is input, and outputs the signal to the count value distribution data processing unit 133 in step S127. When the distribution data table acquisition signal TS2 is input, the count value distribution data processing unit 133 outputs the count value distribution data table CT to the defect correction processing unit 135 in step S128.

In step S129, the defect correction processing unit 135 specifies the defect region in the count value distribution data table CT according to the defect region information DJ. The defect correction processing unit 135 then corrects the count value of the defect region in the count value distribution data table CT in accordance with the count value in the normal measurement region, and generates the corrected count value distribution data table CCT. The defect correction processing unit 135 outputs the corrected count value distribution data table CCT to the control GUI 101. In step S130, the control GUI 101 displays the corrected count value distribution data table CCT.

The analysis device 10 and the analysis method according to the first embodiment set the gate shift amount $\Delta\phi a$ for each measurement radial position (track), and shift the gate signals GS by the gate shift amount $\Delta\phi a$ in the respective measurement radial positions in the rotating direction of the specimen analysis disc 10. The analysis device 100 and the analysis method according to the first embodiment divide the reaction region 14 by the unit gate shift amount $\Delta\phi ua$ in the respective measurement radial positions in the rotating direction of the specimen analysis disc 10 so as to define a plurality of divided regions DR.

Figure 11A:
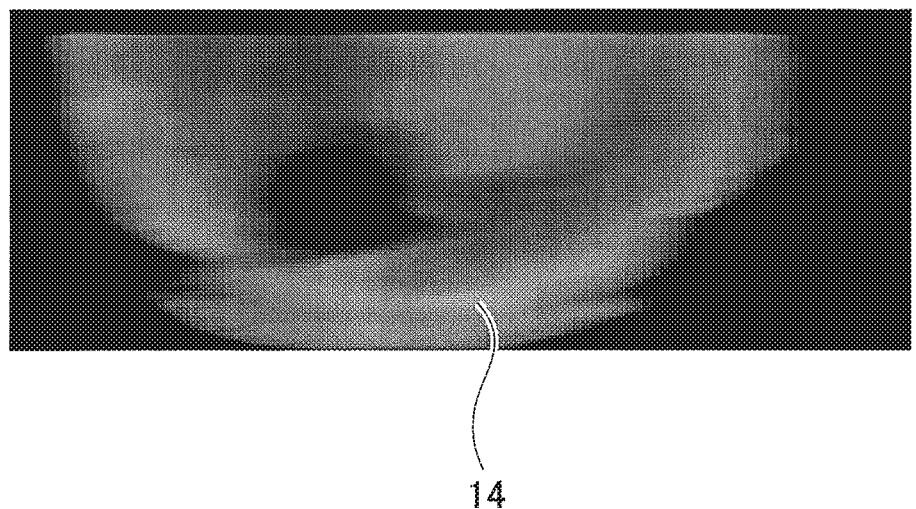
FIG. 11A is a view showing a count value distribution of the reaction region in the case in which the gate signals are shifted in the respective measurement radial positions in the rotating direction of the specimen analysis disc.
Figure 11B:
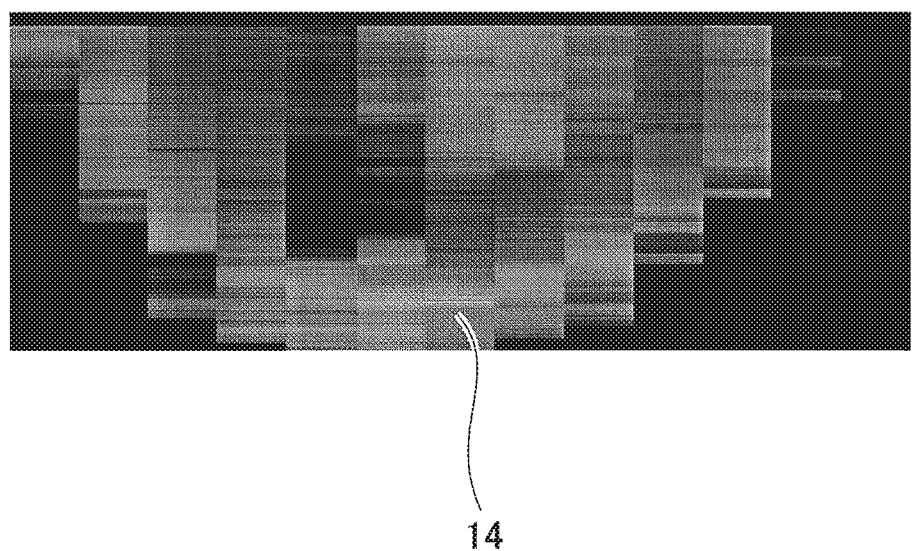
FIG. 11B is a view illustrating a comparative example, showing a count value distribution of the reaction region in the case in which the gate signals are not shifted in the respective measurement radial positions in the rotating direction of the specimen analysis disc.

FIG. 11A is a view showing a par of a count value distribution of the reaction region 14 in the case in which the gate signals GS are shifted in the respective measurement radial positions in the rotating direction of the specimen analysis disc 10 as shown in FIG. 6A. FIG. 11B is a view illustrating a comparative example, showing apart of a count value distribution of the reaction region 14 in the case in which the gate signals GS are not shifted in the respective measurement radial positions in the rotating direction of the specimen analysis disc 10 as shown in FIG. 6B.

The analysis device 100 and the analysis method according to the first embodiment set the count values in the divided regions DR based on the count values of the gate signals GS. Accordingly, an increase in circuit scale is avoided, and the measurement resolution in the rotating direction of the specimen analysis disc can be improved, as shown in FIG. 11A.

Second Embodiment

Figure 12:
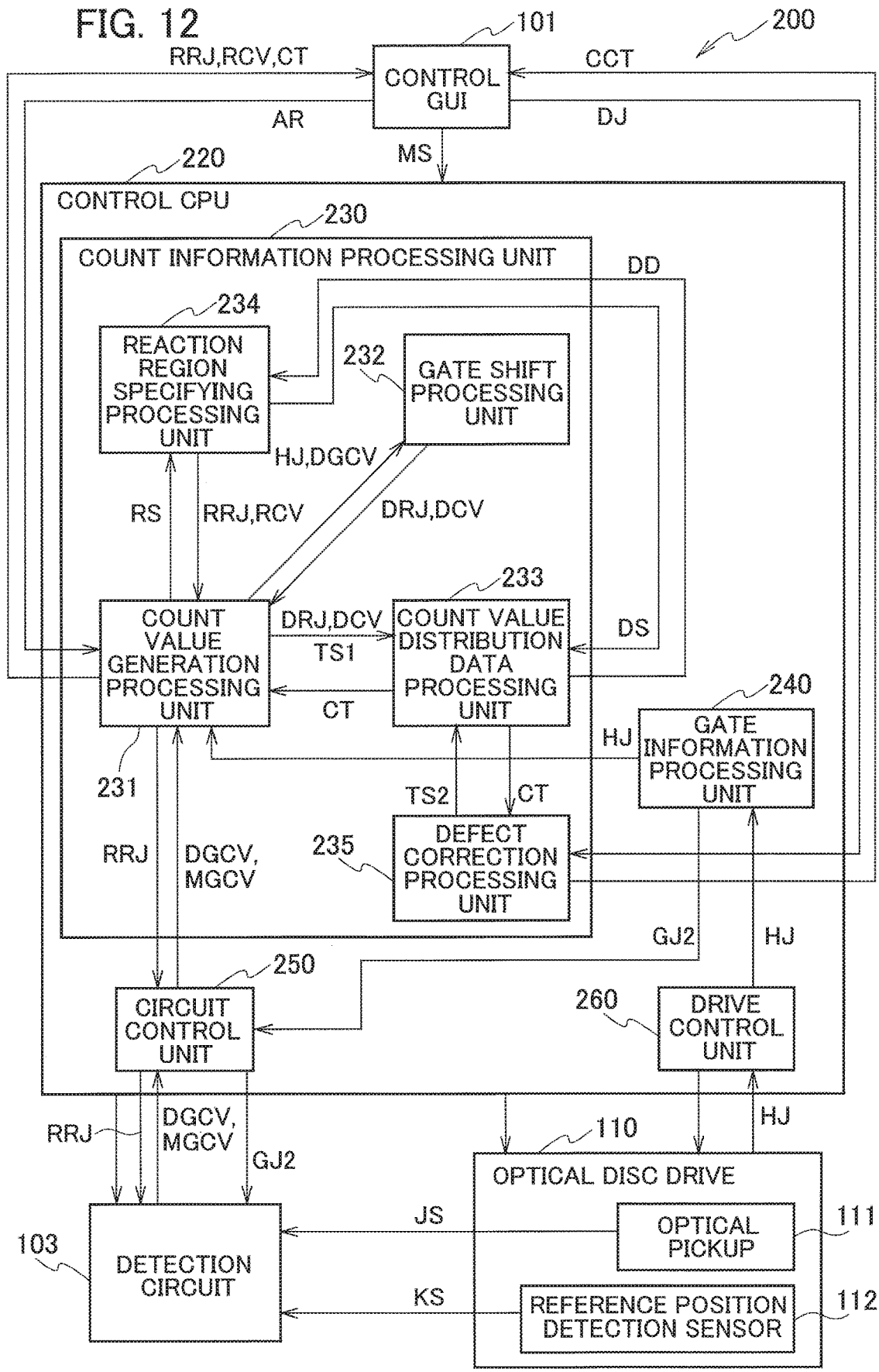
FIG. 12 is a configuration diagram showing an analysis device according to a second embodiment.
Figure 13:
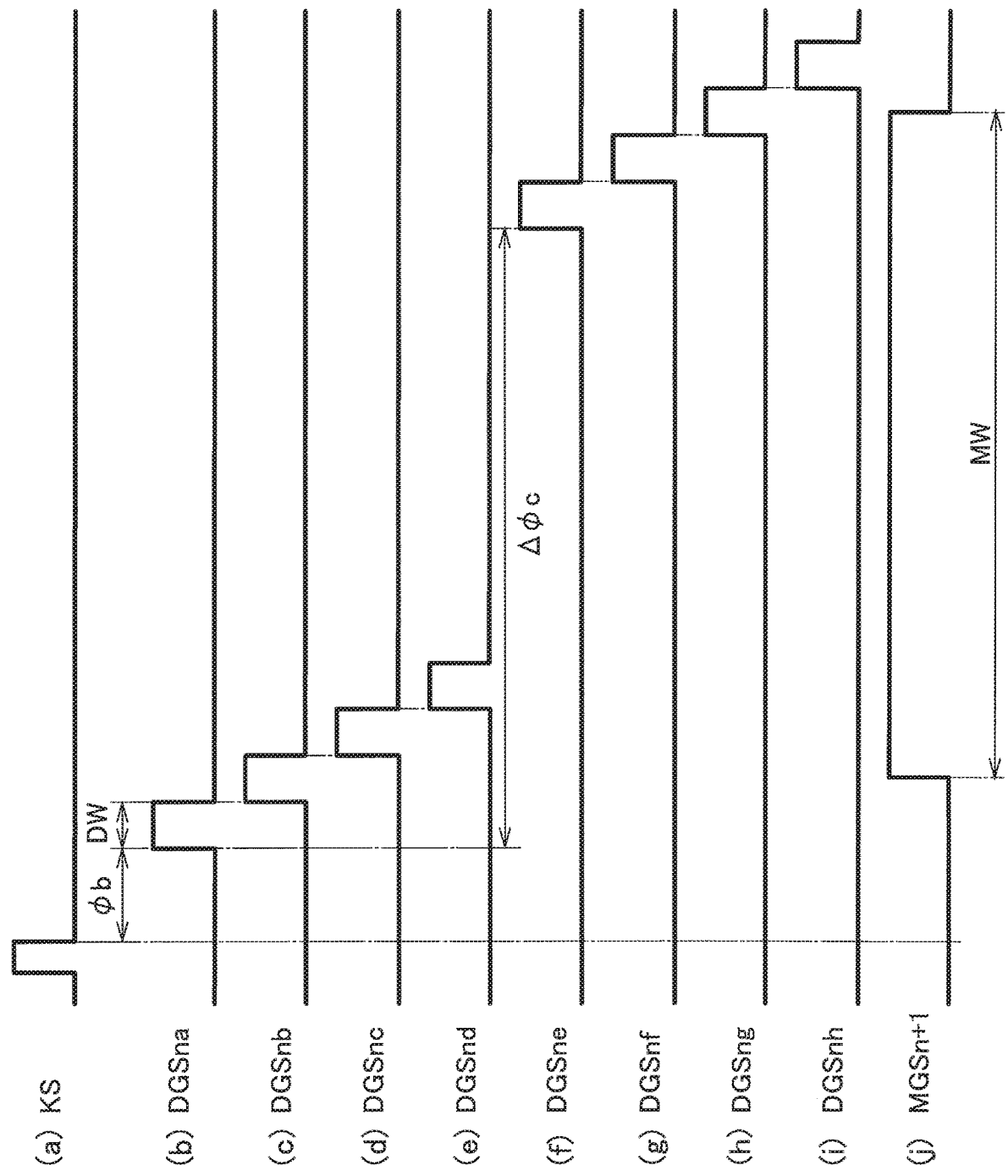
FIG. 13 is a view showing a relationship between a reference position detection signal, distribution gate signals, and a measurement gate signal.
Figure 14:
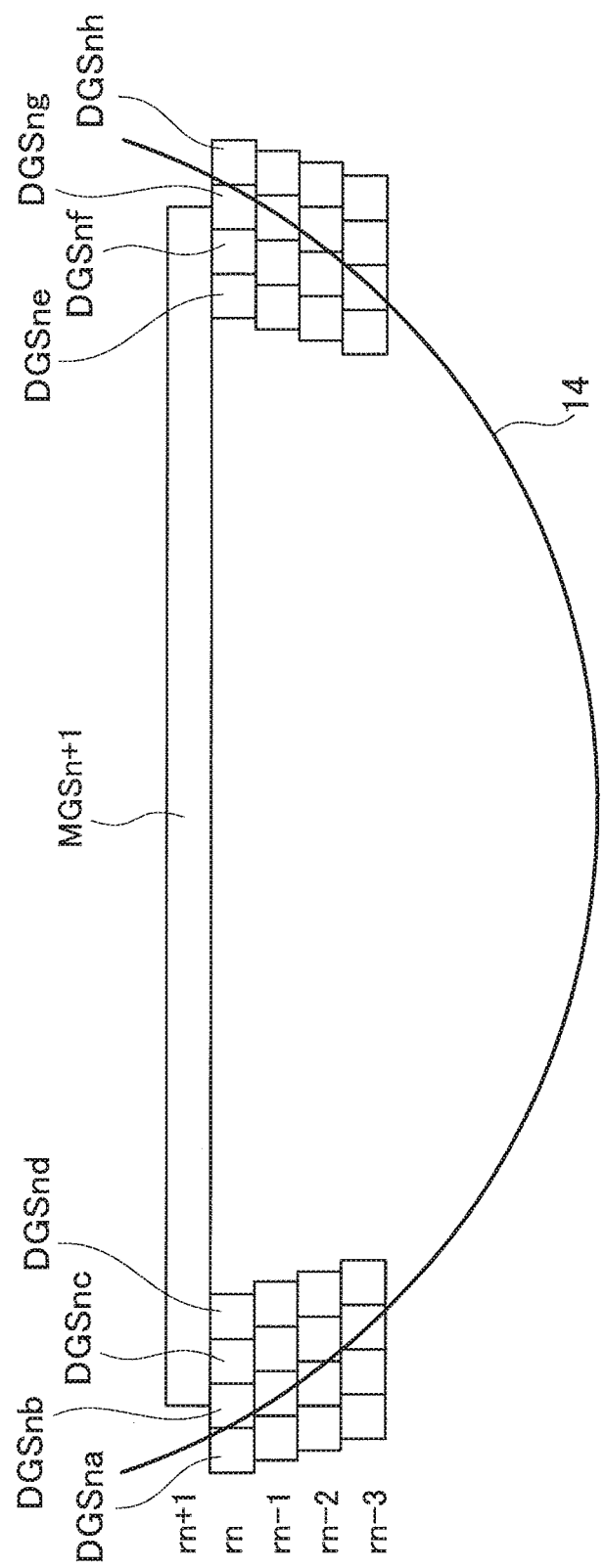
FIG. 14 is a view showing a relationship between the distribution gate signals and the measurement gate signal.

An analysis device according to a second embodiment is described below with reference to FIG. 12 to FIG. 14. The same elements as in the analysis device 100 according the first embodiment are indicated by the same reference numerals for brevity. As shown in FIG. 12, the analysis device 200 includes the control GUI 101, a control CPU 220, the detection circuit 103, and the optical disc drive 110. The control GUI 101 receives an instruction by a user to output a startup command signal MS to the control CPU 220. The control CPU 220 starts up the detection circuit 103 and the optical disc drive 110 when the startup command signal MS is input.

The control CPU 220 includes a count information processing unit 230, a gate information processing unit 240, a circuit control unit 250, and a drive control unit 260. The count information processing unit 230, the gate information processing unit 240, the circuit control unit 250, and the drive control unit 260 may each be composed of software executed by the control CPU 220 or composed of hardware such as a circuit.

The count information processing unit 230 includes a count value generation processing unit 231, a gate shift processing unit 232, a count value distribution data processing unit 233, a reaction region specifying processing unit 234, and a defect correction processing unit 235. The count value generation processing unit 231, the gate shift processing unit 232, the count value distribution data processing unit 233, the reaction region specifying processing unit 234, and the defect correction processing unit 235 may each be composed of aware executed by the control CPU 220 or composed of hardware such as a circuit. The drive control unit 260 executes the same control processing as the drive control unit 160.

The optical disc drive 110 detects a measurement radial position for the optical pickup 111 in the specimen analysis disc 10 to generate measurement radial positional information HJ, and outputs the information to the count value generation processing unit 231 via the drive control unit 260 and the gate information processing unit 240.

The gate information processing unit 240 generates, based on the measurement radial positional information HJ, gate information GJ2 including a reference shift amount $\phi b$, a distribution gate shift amount $\Delta\phi b$, a shift adjustment amount $\Delta\phi c$, a phase difference $\phi b+\Delta\phi b$, and two kinds of gate widths W which are a distribution gate width DW and a measurement gate width MW, and outputs the gate information GJ2 to the circuit control unit 250. The reference shift amount $\phi b$, the distribution gate shift amount $\Delta\phi b$, the shift adjustment amount $\Delta\phi c$, the phase difference $\phi b+\Delta\phi b$, the distribution gate width DW, and the measurement gate width MW will be described below. The circuit control unit 250 outputs the gate information GJ2 to the detection circuit 103.

The detection circuit 103 generates two kinds of gate signals GS which are a distribution gate signal DGS and a measurement gate signal MGS according to the gate information GJ2. The detection circuit 103 synchronizes the timing of the distribution gate signal DGS and the measurement gate signal MGS with the timing of the light reception detection signal JS on the basis of the reference position detection signal KS output from the reference position detection sensor 112. A method of generating distribution gate signals DGS and measurement gate signals MGS will be described below.

The detection circuit 103 extracts nanoparticle pulse signals BS from the light reception detection signal JS per each distribution gate signal DGS and measurement gate signal MGS. The detection circuit 103 counts the extracted nanoparticle pulse signals BS, generates a count value DGCV of the corresponding distribution gate signal DGS and a count value MGCV of the corresponding measurement gate signal MGS, and sequentially outputs the respective values per distribution gate signal DGS and measurement gate signal MGS to the circuit control unit 250. The circuit control unit 250 sequentially outputs, to the count value generation processing unit 231, the respective count values DGCV and MGCV per distribution gate signal DGS and measurement gate signal MGS.

The method of generating each distribution gate signal DGS and measurement gate signal MGS is described below with reference to FIG. 13 and FIG. 14. The gate information processing unit 240 sets the distribution gate width DW of each distribution gate signal DGS in each measurement radial position (track) of the specimen analysis disc 10. The distribution gate width DW is determined according to the rotation number of the specimen analysis disc 10 in the respective measurement radial positions. When the specimen analysis disc 10 is rotated at a constant linear velocity, the distribution gate widths DW in the respective measurement radial positions are set to be the same.

The gate information processing unit 240 sets, as the reference shift amount $\phi b$, a period of time from a point at which the reference position defining portion 11 is detected to a point at which the first distribution signal DGSn rises in a measurement radial position rn corresponding to a track TRn (n is the track number), based on the reference position detection signal KS. For example, the gate information processing unit 240 sets, as the reference shift amount $\phi b$, the period of time from the fall of the reference position detection signal KS to the rise of the first distribution gate signal DGSna, as shown in FIG. 13.

The gate information processing unit 240 sets the distribution gate shift amount $\Delta\phi b$ and the phase difference $\phi b + \Delta\phi b$ for each measurement radial position (track). The gate information processing unit 240 sets the distribution gate shift amount $\Delta\phi b$ and the phase difference $\phi b + \Delta\phi b$ in the respective measurement radial positions so that the distribution gate signals DGS are shifted by DW/m, (m=4 in this embodiment) in the respective measurement radial positions in the rotating direction of the specimen analysis disc 10. The distribution gate shift amount $\Delta\phi b$ is set in a manner similar to the gate shift amount $\Delta\phi a$. In particular, the gate information processing unit 240 sets the distribution gate shift amount $\Delta\phi b$ so as to divide the distribution gate width DW into four.

The detection circuit 103 generates the distribution gate signals DGS based on the reference position detection signal KS and the gate information GJ2. The detection circuit 103 generates a distribution gate signal DGSna which raises after the fall of the reference position detection signal KS with a delay of the reference shift amount $\phi b$ in the measurement radial position rn, for example, and sequentially generates gate signals DGSnb, DGSnc, and DGSnd. The detection circuit 103 further generates a distribution gate signal DGSne which raises after the fall of the reference position detection signal KS with a delay of the reference shift amount $\phi b$+the shift adjustment amount $\Delta\phi c$ in the measurement radial position rn, for example, and sequentially generates gate signals DGSnf, DGSng, and DGSnh.

The distribution gate signals DGS are used for specifying the position of the reaction region 14. The reference shift amount $\phi b$ and the shift adjustment amount $\Delta\phi c$ are set for each measurement radial position so that the distribution gate signals DGS correspond to the outer circumference of the designed position of the reaction region 14. As shown in FIG. 14, the distribution gate signals DGSna to DGSnd are set to correspond to one side of the outer circumference of the reaction region 14 (the outer circumference on the left side in FIG. 14) in the measurement radial position rn. The distribution gate signals DGSne to DGSnh are set to correspond to the other side of the outer circumference of the reaction region 14 (the outer circumference on the right side in FIG. 14) in the measurement radial position rn. The distribution gate signals DGS are used for specifying the position of the reaction region 14.

The detection circuit 103 generates the distribution gate signals DGS shifted by the distribution gate shift amount $\Delta\phi b$ in the respective measurement radial positions in the rotating direction of the specimen analysis disc 10. The distribution gate signals DGS are generated by the same generating method as the gate signals GS.

The detection circuit 103 sequentially outputs the distribution count values DGCV of the corresponding distribution gate signals DGS to the count value generation processing unit 231 via the circuit control unit 250 per distribution gate signal DGS. The detection circuit 103 sequentially outputs the count values MGCV of the corresponding measurement gate signals SAGS to the count value generation processing unit 231 via the circuit control unit 250 per measurement gate signal MGS. The count value generation processing unit 231 outputs the measurement radial positional information HJ to the gate shift processing unit 232, and sequentially outputs the count values DGCV of the corresponding distribution gate signals DGS to the gate shift processing unit 232 per distribution gate signal DGS. The count value generation processing unit 231 stores the count values MGCV per measurement radial position.

The gate shift processing unit 232 divides each gate signal-corresponding region GR of the corresponding distribution gate signal DGS by a unit distribution gate shift amount $\Delta\phi ub$ ($\Delta\phi ub$=DW/m, m=4 in this embodiment) in each measurement radial position in the rotating direction of the specimen analysis disc 10, so as to define a plurality of divided regions DR. The gate shift processing unit 232 sets a count value DCV in each divided region DR. The divided regions DR and the count values DCV are set by the same setting method as the divided regions DR and the count values DCV in the first embodiment.

The gate shift processing unit 232 outputs positional information (for example, central position coordinate information) DRJ of the respective divided regions DR and the count values DCV in the respective divided regions DR to the count value generation unit 231. The count value generation unit 231 outputs the positional information DRJ of the respective divided regions DR and the count values DCV in the respective divided regions DR to the count value distribution data processing unit 233. The count value distribution data processing unit 233 stores the count values DCV of the respective divided regions DR in the count value distribution data table CT in accordance with the positional information DRJ of the respective divided regions DR and the count values DCV in the respective divided regions DR.

The count value generation processing unit 231 determines whether the measurement of each measurement radial position is completed according to the measurement radial positional information HJ. When the measurement is determined to be completed, the count value generation processing unit 231 generates a reaction region specifying signal RS for each measurement radial position, and sequentially outputs the signal to the reaction region specifying processing unit 234.

The reaction region specifying processing unit 234 generates a distribution data acquisition signal DS based on the reaction region specifying signal RS and outputs the signal to the count value distribution data processing unit 233. The count value distribution data processing unit 233 outputs, to the reaction region specifying processing unit 234, the count values DCV in the respective divided regions DR in the corresponding measurement radial position stored in the count value distribution data table CT as count value distribution data DD in accordance with the distribution data acquisition signal DS.

When the count value distribution data DD is input, the reaction region specifying processing unit 234 scans the entire measurement region 16 with a filter having a shape greater in length than the diameter of the reaction region 14 in design and greater in width than the divided regions DR in the radial direction of the specimen analysis disc 10, and determines a position where the filter has the largest count value. The reaction region specifying processing unit 234 specifies the position of the reaction region 14 (for example, a central position coordinate) in each measurement radial position in accordance with the determination result, and generates the positional information RRJ of the reaction region 14 for each measurement radial position. Any other method that can specify the position of the reaction region 14 may be used instead.

The reaction region specifying processing unit 234 outputs the positional information RRJ of the reaction region 14 to the detection circuit 103 via the count value generation processing unit 231 and the circuit control unit 250 per measurement radial position. The detection circuit 103 generates the measurement gate signal MGS based on the reference position detection signal KS, the gate information GJ2, and the positional information RRJ. When positional information RRJn generated in accordance with the distribution gate signal DGSn in the measurement radial position rn is input to the detection circuit 103, the detection circuit 103 generates a measurement gate signal MGSn+1 in the measurement radial position rn+1 subsequently measured, in accordance with the reference position detection signal KS, the gate information GJ2, and the positional information RRJ.

In particular, when the detection circuit 103 generates each distribution gate signal DGSn+1 and measurement gate signal MGSn+1 in the subsequent measurement radial position rn+1, the detection circuit 103 generates the measurement gate signal MGSn+1 having a measurement gate width MW corresponding to the reaction region 14 in the measurement radial position rn+1 in accordance with the positional information RRJn of the reaction region 14 in the previous measurement radial position rn. The measurement gate signal MGS is used for counting the number of nanoparticles 15 in the reaction region 14 and the number of detection target substances.

The count value generation processing unit 231 determines whether the measurement of the reaction region 14 is completed according to the measurement radial positional information HJ. When the measurement is determined to be completed, the count value generation processing unit 231 sums up the count values MGCV in all of the measurement radial positions so as to determine the count value RCV in the reaction region 14. The count value RCV in the reaction region corresponds to the number of nanoparticles 15 captured in the reaction region 14 and the number of detection target substances specifically bound to the nanoparticles 15.

When the measurement is determined to be completed, the count value generation processing unit 231 generates a distribution data table acquisition signal TS1 and outputs the signal to the count value distribution data processing unit 233. The count value distribution data processing unit 233 outputs the count value distribution data table CT to the count value generation processing unit 231 when the distribution data table acquisition signal TS1 is input.

When the measurement is determined to be completed, the count value generation processing unit 231 generates a reaction region specifying signal RS and outputs the signal to the reaction region specifying processing unit 234. When the reaction region specifying signal RS is input, the reaction region specifying processing unit 234 generates a distribution data acquisition signal DS and outputs the signal to the count value distribution data processing unit 233. When the distribution data acquisition signal DS is input, the count value distribution data processing unit 233 outputs, to the reaction region specifying processing unit 234, the count values DCV in the respective divided regions DR stored in the count value distribution data table CT as count value distribution data DD.

The reaction region specifying processing unit 234 specifies the position of the reaction region 14 (for example, the central position coordinate) in accordance with the detection result in each measurement radial position to generate the positional information RRJ of the reaction region 14, and outputs the information to the count value generation processing unit 231.

When an acquisition request AR for the measurement result is made by the control GUI 101, the count value generation processing unit 231 outputs, to the control GUI 101, the positional information RRJ of the reaction region 14, the count value RCV in the reaction region 14, and the count value distribution data table CT.

The control GUI 101 displays a count value distribution of the reaction region 14 obtained by associating the reaction region 14 with the count value distribution data table CT or displays the count value RCV of the reaction region 14.

Figure 15A:
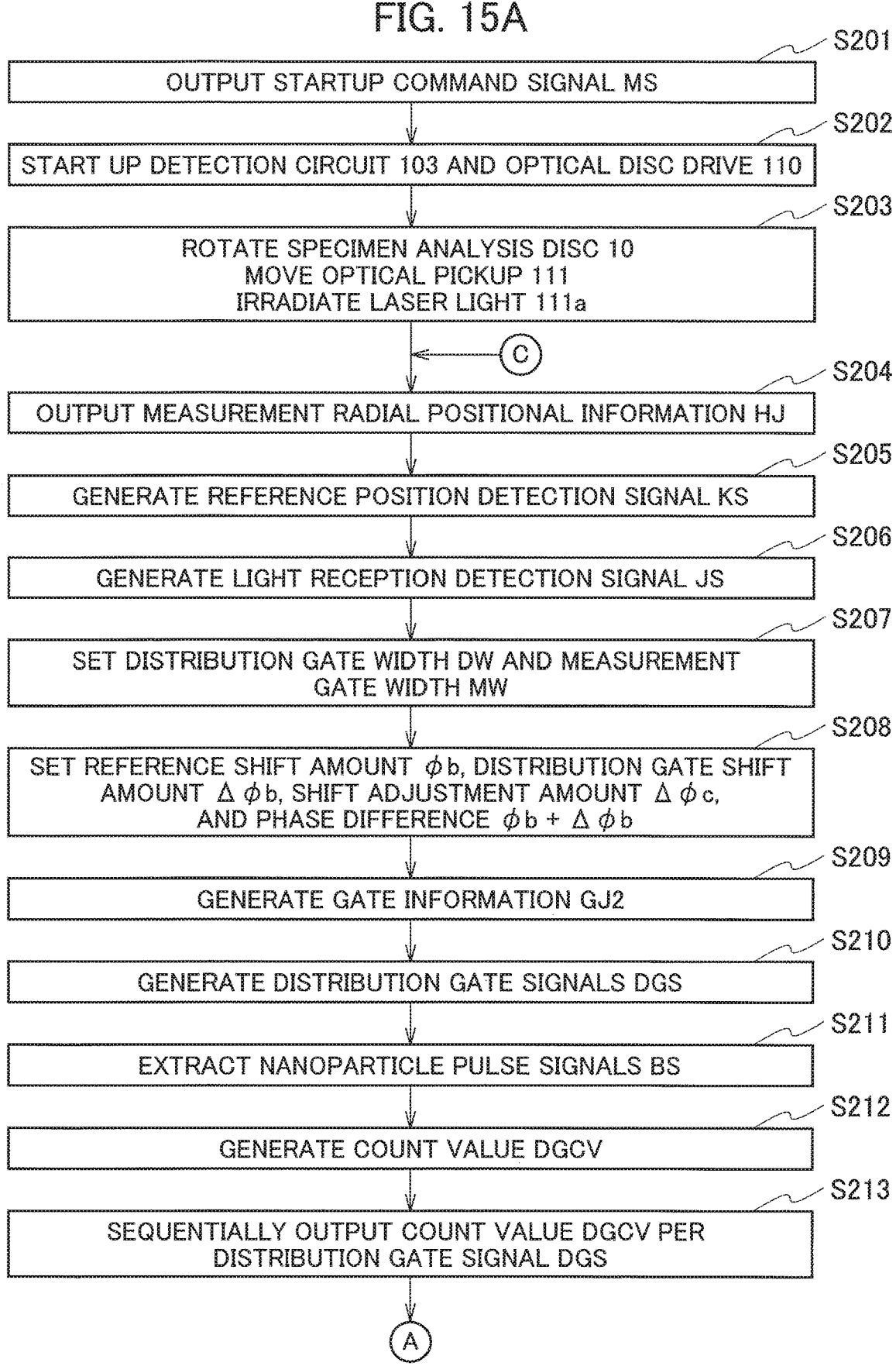
FIG. 15A is a flowchart showing an analysis method of analyzing nanoparticles in a reaction region by the analysis device according to the second embodiment.
Figure 15B:
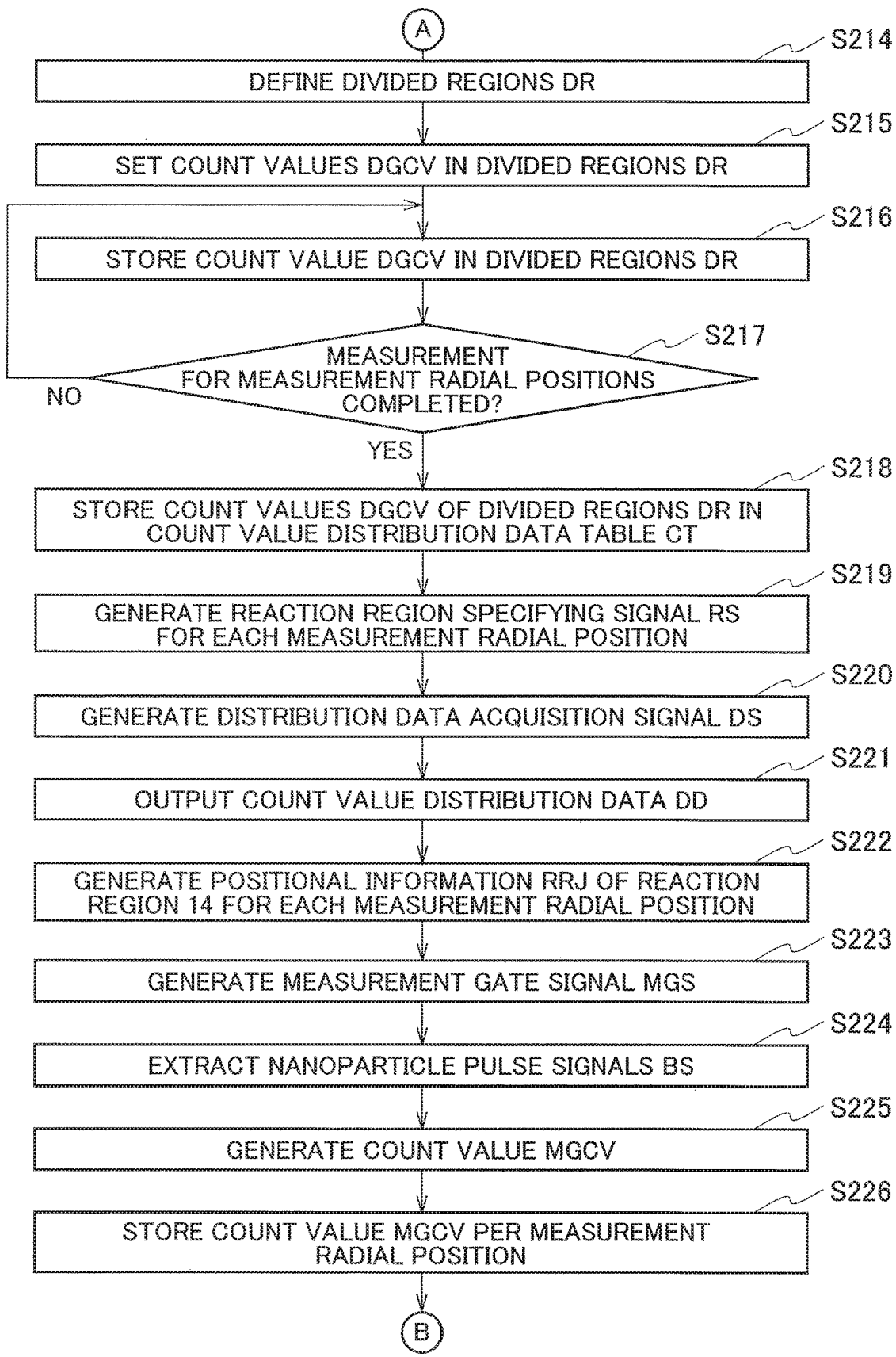
FIG. 15B is a flowchart showing the analysis method of analyzing nanoparticles in the reaction region by the analysis device according to the second embodiment.
Figure 15C:
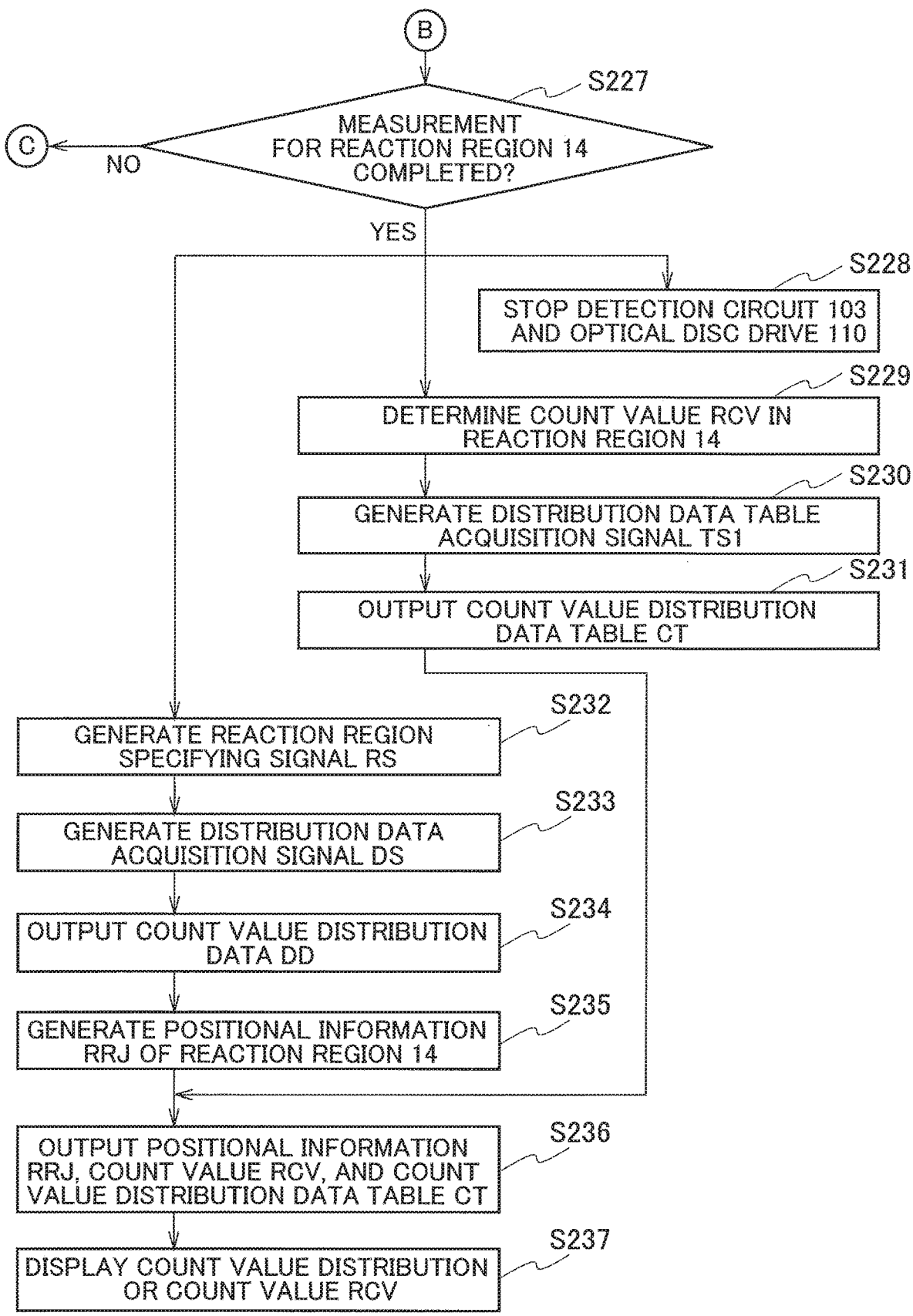
FIG. 15C is a flowchart showing the analysis method of analyzing nanoparticles in the reaction region by the analysis device according to the second embodiment.

An analysis method by the analysis device 200 according to the second embodiment is described below with reference to the flowcharts shown in FIG. 15A, FIG. 15B, and FIG. 15C. In step S201 shown in FIG. 15A, the control GUI 101 outputs the startup command signal MS to the control CPU 220 in accordance with the instruction by the user. When the startup command signal MS is input, the control CPU 220 starts up the detection circuit 103 and the optical disc drive 110 in step S202.

In step S203, the drive control unit 260 of the control CPU 220 controls the optical disc drive 110 to control the rotation of the specimen analysis disc 10. The drive control unit 260 of the control CPU 220 further controls the optical disc drive 110 to move the optical pickup 111 to the target measurement radial position in the specimen analysis disc 10 and direct the optical pickup 111 to emit the laser light 111a to the specimen analysis disc In step S204, the optical disc drive 110 generates the measurement radial positional information HJ including the measurement radial position for the optical pickup 111 in the specimen analysis disc 10, and outputs the information to the count value generation processing unit 231 via the drive control unit 260 and the gate information processing unit 240. In step S205, the reference position detection sensor 112 detects the reference position defining portion 11 in the specimen analysis disc 10 and generates the reference position detection signal KS. In step S206, the optical pickup 111 receives the reflected light from the specimen analysis disc 10 and generates the light reception detection signal JS.

In step S207, the gate information processing unit 240 sets the distribution gate width DW and the measurement gate width MW for each measurement radial position. The optical disc drive 110 and the gate information processing unit 240 may execute the steps S204 to S206 and step S207 simultaneously.

In step S208, the gate information processing unit 240 sets, as the reference shift amount φb for each measurement radial position (track), the period of time from the point at which the reference position defining portion 11 is detected to the point at which the measurement region 16 reaches the measurement radial position, in accordance with the measurement radial positional information HJ. The gate information processing unit 240 sets the distribution gate shift amount Δφb, the shift adjustment amount Δφc, and the phase difference φb+Δφb for each measurement radial position.

In step S209, the gate information processing unit 240 generates the gate information GJ2 based on the measurement radial positional information HJ, and outputs the gate information GJ2 to the detection circuit 103 via the circuit control unit 250. In step S210, the detection circuit 103 generates the distribution gate signals DGS shifted in the respective measurement radial positions in the rotating direction of the specimen analysis disc 10 on the basis of the reference position detection signal KS and the gate information GJ2.

In step S211, the detection circuit 103 extracts the nanoparticle pulse signals ES from the light reception detection signal JS per distribution gate signal DGS. In step S212, the detection circuit 103 counts the extracted nanoparticle pulse signals ES and generates the count value DGCV of the corresponding distribution gate signal DGS.

In step S213, the detection circuit 103 sequentially outputs the count values DGCV per distribution gate signal DGS to the gate shift processing unit 232 via the circuit control unit 250 and the count value generation processing unit 231. In step S214 shown in FIG. 15E, the gate shift processing unit 232 divides the gate signal-corresponding region GR of the corresponding distribution gate signal DGS by the unit distribution gate shift amount Δφub (Δφub=DW/4) in each measurement radial position in the rotating direction of the specimen analysis disc 10 so as to define a plurality of divided regions DR. In step S215, the gate shift processing unit 232 sets the count values DGCV in the respective divided regions DR.

In step S216, the count value distribution data processing unit 233 successively stores the count values DGCV of the divided regions DR in an internal memory per divided region DR. In step S217, the count value generation processing unit 231 determines whether the measurement of each measurement radial position is completed according to the measurement radial positional information HJ. When the measurement in the respective measurement radial positions is determined not to be completed yet (NO in step S217), the control CPU 220 causes the process to return to step S216.

When the measurement of the respective measurement radial positions is determined to be completed (YES in step S217), the count value generation processing unit 231 stores, in the count value distribution data table CT, the count values DGCV in the respective divided regions DR stored in the internal memory in accordance with the positional information DRJ of the corresponding divided regions DR in step S218. In step S219, the count value generation processing unit 231 generates the reaction region specifying signal RS for each measurement radial position and sequentially outputs the signal to the reaction region specifying processing unit 234.

In step S220, the reaction region specifying processing unit 234 generates the distribution data acquisition signal DS based on the reaction region specifying signal RS, and outputs the generated signal to the count value distribution data processing unit 233. In step S221, the count value distribution data processing unit 233 outputs, to the reaction region specifying processing unit 234, the count values DCV of the respective divided regions DR in the corresponding measurement radial position stored in the count value distribution data table CT as count value distribution data DD.

When the count value distribution data DD is input, the reaction region specifying processing unit 234 scans the entire measurement region 16 with the filter, and determines a position where the filter has the largest count value in step S222. The reaction region specifying processing unit 234 specifies the position of the reaction region 14 (for example, the central position coordinate) in each measurement radial no ion in accordance with the determination result, and generates the positional information RRJ of the reaction region 14 for each measurement radial position. The reaction region specifying processing unit 234 outputs the positional information RRJ of the reaction region 14 to the detection circuit 103 via the count value generation processing unit 231 and the circuit control unit 250 per measurement radial position.

In step S223, the detection circuit 103 generates the measurement gate signal MGS based on the reference position detection signal KS, the gate information GJ2, and the positional information RRJ. When the detection circuit 103 generates each distribution gate signal DGSn±1 and measurement gate signal MGSn+1 in the measurement radial position rn+1, the detection circuit 103 generates the measurement gate signal MGSn+1 based on the positional information RRJn in the previous measurement radial position rn.

In step S224, the detection circuit 103 extracts the nanoparticle pulse signals BS from the light reception detection signal JS per measurement gate signal MGS. In step S225, the detection circuit 103 counts the extracted nanoparticle pulse signals BS and generates the count value MGCV of the corresponding measurement gate signal MGS. The detection circuit 103 sequentially outputs the count values MGCV per measurement gate signal MGS to the count value generation processing unit 231 via the circuit control unit 250. Steps S211 and S212 and steps S224 and S225 are executed simultaneously by the detection circuit 103. In step S226, the count value generation processing unit 231 stores the count value MGCV per measurement radial position.

In step S227, the count value generation processing unit 237 determines whether the measurement of the reaction region 14 is completed according to the measurement radial positional information HJ. When the measurement is determined not to be completed yet (NO in step S227), the control CPU 220 causes the process to return to step S204. When the measurement is determined to be completed (YES in step S227), the control CPU 220 stops the detection circuit 103 and the optical disc drive 110 in step S228.

When the measurement is determined to be completed in step S227, the count value generation processing unit 231 sums up the count values MGCV in all of the measurement radial positions so as to determine the count value RCV in the reaction region 14 in step S229. The count value RCV in the reaction region 14 corresponds to the number of nanoparticles 15 captured in the reaction region 14 and the number of detection target substances specifically bound to the nanoparticles 15.

In step S230, the count value generation processing unit 231 generates the distribution data table acquisition signal TS1 and outputs the signal to the count value distribution data processing unit 233. When the distribution data table acquisition signal TS1 is input, the count value distribution data processing unit 233 outputs the count value distribution data table CT to the count value generation processing unit 231 in step S231.

When the measurement is determined to be completed in step S227, the count value generation processing unit 231 generates the reaction region specifying signal RS and outputs the signal to the reaction region specifying processing unit 234 in step S232. When the reaction region specifying signal RS is input, the reaction region specifying processing unit 234 generates the distribution data acquisition signal DS and outputs the signal to the count value distribution data processing unit 233 in step S233. When the distribution data acquisition signal DS is input, the count value distribution data processing unit 233 outputs, to the reaction region specifying processing unit 234, the count values DCV in the respective divided regions DR stored in the count value distribution data table CT as count value distribution data DD in step S234.

In step S235, the reaction region specifying processing unit 234 specifies the position of the reaction region 14 (for example, the central position coordinate) based on the count value distribution data DD to generate the positional information RRJ of the reaction region 14, and outputs the information to the count value generation processing unit 231.

When the acquisition request AR for the measurement result is made by the control GUI 101, the count value generation processing unit 231 outputs, to the control GUI 101, the positional information RRJ of the reaction region 14, the count value RCV in the reaction region 14, and the count value distribution data table CT in step S236. In step S237, the control GUI 101 displays the count value distribution of the reaction region 14 obtained by associating the reaction region 14 with the count value distribution data table CT or displays the count value RCV of the reaction region 14.

The analysis device 200 and the analysis method according to the second embodiment generate two kinds of gate signals GS which are the distribution gate signal DGS and the measurement gate signal MGS. The distribution gate signal DGS is used for specifying the position of the reaction region 14. The measurement gate signal MGS is used for counting the number of nanoparticles 15 in the reaction region 14 and the number of detection target substances.

The analysis device 200 and the analysis method according to the second embodiment set the distribution gate shift amount Δϕb for each measurement radial position (track). The analysis device 200 and the analysis method according to the second embodiment shift the distribution gate signals DGS by the distribution gate shift amount Δϕb in the respective measurement radial positions in the rotating direction of the specimen analysis disc 10. The analysis device 200 and the analysis method according to the second embodiment divide the reaction region 14 by the unit distribution gate shift amount Δϕub in the respective measurement radial positions in the rotating direction of the specimen analysis disc 10 so as to define a plurality of divided regions DR.

The analysis device 200 and the analysis method according to the second embodiment generate the distribution gate signals DGS corresponding to the outer circumference of the designed position of the reaction region 14, and set the count values of the divided regions DR based on the count values of the distribution gate signals DGS. Accordingly, an increase in circuit scale is avoided, and the measurement resolution in the rotating direction of the specimen analysis disc 10 can be improved.

The analysis device 200 and the analysis method according to the second embodiment generate the measurement gate signal MGSn+1 having a measurement gate width MW corresponding to the reaction region in the measurement radial position rn+1 in accordance with the positional information RRJn of the reaction region 14 in the previous measurement radial position rn. The analysis device 200 and the analysis method according to the second embodiment thus can count the number of nanoparticles 15 in the reaction region 14 and the number of detection target substances accurately due to the measurement gate signal MGSn+1 with the measurement gate width MW corresponding to the reaction region 14.

It should be understood that the present invention is not intended to be limited to the embodiments described above, and various modifications will be apparent to those skilled in the art without departing from the scope of the present invention.

The analysis device 100 and the analysis method according to the first embodiment set the unit gate shift amount Δϕua so as to divide the gate width W into three (m=3), and the analysis device 200 and the analysis method according to the second embodiment set the unit distribution gate shift amount Δϕub so as to divide the distribution gate width DW into four (m=4). When the unit gate shift amount Δϕua and the unit distribution gate shift amount Δϕub are set so as to divide the gate width W and the distribution gate width DW each into the number m, the measurement resolution in the rotating direction of the specimen analysis disc is further increased as the number m increases, and an increase in circuit scale is further prevented as the number m decreases. The number m for division is therefore not limited to that described in the analysis device 100 or 200 or the analysis method according the first or second embodiment, but is determined as appropriate depending on the specifications of design.

The embodiments can provide the analysis device and the analysis method with an increase in circuit scale avoided and the measurement resolution in the rotating direction of the specimen analysis disc improved.

What is claimed is:

1. An analysis device comprising:
a drive control circuit;
an optical disc drive including an optical pickup and a reference position detection sensor,
wherein the optical disc drive is configured to rotate a circular specimen analysis disc,
wherein the drive control circuit is configured to control the rotation of the circular specimen analysis disc,
wherein the optical disc drive is configured to move the optical pickup in a radial direction of the specimen analysis disc,
wherein the optical disc drive is configured to direct the optical pickup to emit laser light to a reaction region formed in the specimen analysis disc with nanoparticles captured,
wherein the optical pickup is configured to generate a light reception detection signal based on reception of light reflected from the specimen analysis disc after emitting the laser light,
wherein the reference position detection sensor is configured to generate a reference position detection signal based on detection of a reference position defining portion formed in the specimen analysis disc, wherein the optical disc drive is configured to generate measurement radial positional information based on detection of a measurement radial position which is a position of the optical pickup in the radial direction of the specimen analysis disc, wherein the drive control circuit is further configured to:
receive the measurement radial positional information from the optical disc drive; and
transmit the measurement radial positional information to a gate information processing unit, wherein the gate information processing unit is configured to generate gate information including a phase difference and a gate width based on the measurement radial positional information, wherein the phase difference includes a reference shift amount and a gate shift amount, wherein the reference shift amount is a fixed value, and wherein the gate shift amount is a variable value depending on the measurement radial position and being equal to a positive integral multiple of a unit gate shift amount;

a detection circuit configured to:

generate a gate signal with the gate width, which raises with the phase difference after falling of the reference position detection signal, in accordance with the reference position detection signal and the gate information, synchronize timing between the gate signal and the light reception detection signal, extract nanoparticle pulse signals from the light reception detection signal during the gate width of the gate signal by detecting and discriminating pulse waveforms in the light reception detection signal, the nanoparticle pulse signals being generated by the light reflected by the nanoparticles captured in the reaction region formed in the specimen analysis disc, and count the nanoparticle pulse signals to generate a count value of the gate signal; and a gate shift processing unit configured to:

divide a gate signal-corresponding region on the specimen analysis disc corresponding to the gate signal, by the unit gate shift amount in the rotating direction of the specimen analysis disc to define a plurality of divided regions, and generate positional information of the divided regions based on the measurement radial positional information and set count values of the divided regions based on the count value of the gate signal.

2. The analysis device according to claim 1, wherein the gate information processing unit:

divides a measurement region on the specimen analysis disc including the reaction region into two or more in the rotating direction of the specimen analysis disc, to generate two or more regions, and sets each region as the gate signal-corresponding region, and divides the gate width of the gate signal into two or more to generate two or more widths, and sets each of the widths as the unit gate shift amount.

3. The analysis device according to claim 1, wherein the gate shift processing unit sets the count values of the divided regions based on the count value in the gate signal corresponding to the gate signal-corresponding region including the divided regions and count values of gate signals corresponding to gate signal-corresponding regions adjacent to the divided regions.

4. The analysis device according to claim 1, further comprising:

a count value distribution data processing unit configured to store the count values of the divided regions in a count value distribution data table in accordance with the positional information of the divided regions; and a reaction region specifying processing unit configured to specify a position of the reaction region based on the count values of the divided regions stored in the count value distribution data table to determine a count value in the reaction region.

5. The analysis device according to claim 4, further comprising a count value generation processing unit, wherein:

the reaction region specifying processing unit specifies the position of the reaction region in each measurement radial position, and the detection circuit generates a distribution gate signal as the gate signal and a measurement gate signal, the distribution gate signal shifted by the gate shift amount in each measurement radial position in the rotating direction of the specimen analysis disc, and the measurement gate signal having a gate width corresponding to the reaction region generated in accordance with positional information of the reaction region in a measurement radial position previous to the measurement radial position in which the distribution gate signal is generated;

the reaction region specifying processing unit specifies the position of the reaction region based on the distribution gate signal; and the count value generation processing unit sums up a count value in the measurement gate signal in all of the measurement radial positions so as to determine the count value in the reaction region.

* * * * *